(12) United States Patent
Nagai et al.

(10) Patent No.: US 10,478,045 B2
(45) Date of Patent: Nov. 19, 2019

(54) FLEXIBLE TUBE FOR AN ENDOSCOPE, ADHESIVE FOR AN ENDOSCOPE, ENDOSCOPE-TYPE MEDICAL DEVICE, AS WELL AS METHOD OF PRODUCING A FLEXIBLE TUBE FOR AN ENDOSCOPE AND METHOD OF PRODUCING AN ENDOSCOPE-TYPE MEDICAL DEVICE

(71) Applicant: FUJIFILM Corporation, Tokyo (JP)

(72) Inventors: Takayasu Nagai, Kanagawa (JP); Yoshihiro Nakai, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 810 days.

(21) Appl. No.: 14/867,888

(22) Filed: Sep. 28, 2015

(65) Prior Publication Data

US 2016/0088998 A1    Mar. 31, 2016

(30) Foreign Application Priority Data

Sep. 29, 2014  (JP) ................................. 2014-199427

(51) Int. Cl.
 *A61B 1/00* (2006.01)
 *A61B 1/005* (2006.01)

(52) U.S. Cl.
 CPC .......... *A61B 1/0011* (2013.01); *A61B 1/0055* (2013.01)

(58) Field of Classification Search
 CPC ....... A61B 1/0011; A61B 1/005; C08G 18/12; C08G 18/3228; C08G 18/4018
 USPC ................................. 428/35.1, 34.7
 See application file for complete search history.

(56) References Cited

U.S. PATENT DOCUMENTS

2005/0288545 A1* 12/2005 Matsumoto .......... A61B 1/0011
                                                    600/101

FOREIGN PATENT DOCUMENTS

| CN | 102688013 A | 9/2012 |
|---|---|---|
| EP | 2366325 A1 | 9/2011 |
| EP | 2484269 A1 | 8/2012 |
| JP | 61-046923 A | 3/1986 |
| JP | 7-330856 A | 12/1995 |
| JP | 2001-275936 A | 10/2001 |
| JP | 2001-346754 A | 12/2001 |
| JP | 2003-129023 A | 5/2003 |
| JP | 2005-287774 A | 10/2005 |
| WO | 2006/098322 A1 | 9/2006 |
| WO | 2007/087987 A1 | 8/2007 |
| WO | 2015/081486 A1 | 6/2015 |

OTHER PUBLICATIONS

Communication dated Feb. 1, 2016, issued by the European Patent Office in corresponding European Application No. 15187346.0.
(Continued)

*Primary Examiner* — Laura C Powers
(74) *Attorney, Agent, or Firm* — Sughrue Mion, PLLC

(57) ABSTRACT

A flexible tube for an endoscope, containing: a tubular flexible tube substrate material having a flexibility; and a resin layer covering the flexible tube substrate material, in which the resin layer is adhered to the flexible tube substrate material with an adhesive hardened, the adhesive hardened contains an ester-based polyurethane resin, which is a hardened resin of an adhesive for an endoscope, and the adhesive for an endoscope contains an ester-based urethane polymer having a structure represented by a specific formula.

17 Claims, 5 Drawing Sheets

(56) References Cited

OTHER PUBLICATIONS

Communication dated Jan. 3, 2018, issued by the State Intellectual Property Office of People's Republic of China in corresponding Chinese Application No. 201510629211.6.
Communication dated Oct. 18, 2016, from the Japanese Patent Office in counterpart application No. 2014-199427.
Communication dated Jun. 19, 2018 from the State Intellectual Property Office of the P.R.C. in counterpart application No. 201510629211.6.

* cited by examiner

FLEXIBLE TUBE FOR AN ENDOSCOPE, ADHESIVE FOR AN ENDOSCOPE, ENDOSCOPE-TYPE MEDICAL DEVICE, AS WELL AS METHOD OF PRODUCING A FLEXIBLE TUBE FOR AN ENDOSCOPE AND METHOD OF PRODUCING AN ENDOSCOPE-TYPE MEDICAL DEVICE

CROSS-REFERENCE TO RELATED APPLICATION

The present application claims priority under 35 U.S.C. § 119 to Japanese Patent Application No. 2014-199427 filed in Japan on Sep. 29, 2014. The above application is hereby expressly incorporated by reference, in its entirety, into the present application.

TECHNICAL FIELD

The present invention relates to a flexible tube for an endoscope, an adhesive for an endoscope, and an endoscope-type medical device, as well as a method of producing a flexible tube for an endoscope and a method of producing an endoscope-type medical device.

BACKGROUND ART

An endoscope is a medical device for observing inside of a body cavity of a subject.

For a reason that the endoscope is inserted into the inside of the body cavity to use, an endoscope, which does not injure organs and also does not inflict a pain or uncomfortable feeling on the subject, is required. Therefore, as to a flexible tube which constitutes an insertion portion of the endoscope, a spiral tube, formed in such a way that a soft and inflective a metal strip is wound spirally, is adopted. Further, the flexible tube for an endoscope is designed in such a way that the flexible tube is covered with a flexible resin so as not to stimulate or not to damage to a surface of an esophagus, an intestine, and the like.

Further, the endoscope is used repetitively. Therefore, as a way to counter pathogenic bacteria, a flexible tube for an endoscope having an excellent antibacterial property, which contains an antibacterial extract in its outer skin, is proposed (see Patent Literature 1).

In another technical field, for example, as an adhesive used in construction at a building site, one-liquid reactive type polyurethane resin-based adhesive whose adherence property is less likely to vary due to an outside air temperature, is proposed (see Patent Literature 2).

CITATION LIST

Patent Literature

Patent Literature 1: JP-A-2001-275936 ("JP-A" means unexamined published Japanese patent application)
Patent Literature 2: JP-A-2003-129023
Patent Literature 3: JP-A-61-46923

SUMMARY OF INVENTION

A flexible tube for an endoscope, containing:
a tubular flexible tube substrate material having a flexibility; and
a resin layer covering the flexible tube substrate material, wherein the resin layer is adhered to the flexible tube substrate material with an adhesive hardened,
wherein the adhesive hardened contains an ester-based polyurethane resin, which is a hardened resin of an adhesive for an endoscope, and
wherein the adhesive for an endoscope contains an ester-based urethane polymer having a structure represented by the following Formula (1):

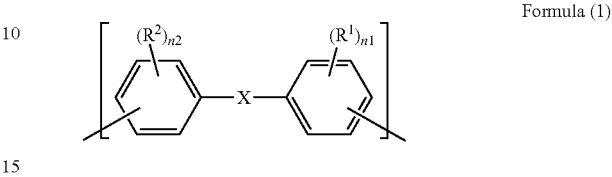

Formula (1)

wherein $R^1$ and $R^2$ each independently represent an alkyl group, an alkoxy group, an alkylthio group, an aryl group, or a halogen atom; n1 and n2 each independently represent an integer of 0 to 4; X represents $-C(R^a)(R^b)-$, $-O-$, $-S-$, $-SO_2-$, $-C(=O)-$, or $-N(R^c)-$; $R^a$ and $R^b$ each independently represent a hydrogen atom, an alkyl group, or an aryl group; $R^c$ represents a hydrogen atom or an alkyl group; and $R^a$ and $R^b$ may be bonded to each other to form a ring, which flexible tube for an endoscope is favorably used for an endoscope-type medical device; a method of producing the flexible tube for an endoscope; a method of producing an endoscope-type medical device; and an adhesive for an endoscope favorably used for the flexible tube for an endoscope.

Technical Problem

A resin of a flexible tube for an endoscope is usually adhered to a substrate material of the flexible tube with an adhesive. However, almost no attempt to improve this adhesive is known. For example, Patent Literature 3 can be cited as one example thereof at most. This literature proposes a flexible tube for an endoscope prepared using an adhesive of a polyester-based urethane resin obtained from toluene diisocyanate as a monomer, for the purpose of improving a bending durability which is required because the flexible tube for an endoscope is bended on a frequent basis.

In this regards, the present inventors have found through their studies that a selection of not only a resin covering the flexible tube for an endoscope but also an adhesive is important, in order to improve a chemical resistance of the above-described flexible tube. Further, along with the improvement of the chemical resistance, it is also important not to deteriorate the properties required for the endoscope, such as improvement in a resilient property associated with operability, flexibility and the like.

In view of the above, the present invention is contemplated for providing: a flexible tube for an endoscope, covered with a resin layer, which exhibits high chemical resistance and high peel strength, and also excellent resilient property and flexibility; an endoscope-type medical device using the same; and an adhesive for an endoscope, which can satisfies various performances to be required for the flexible tube for an endoscope. Further, the present invention is contemplated for providing: a method of producing a flexible tube for an endoscope and a method of producing an endoscope-type medical device, in which thermal stability at the time of molding is improved by using this adhesive for an endoscope, whereby a flexible tube for an endoscope and the endoscope-type medical device can be favorably produced respectively, and each of which has the above-described excellent performances.

Solution to Problem

The above problems of the present invention were solved by the following means.

[1] A flexible tube for an endoscope, comprising:
a tubular flexible tube substrate material having a flexibility; and
a resin layer covering the flexible tube substrate material,
wherein the resin layer is adhered to the flexible tube substrate material with an adhesive hardened,
wherein the adhesive hardened contains an ester-based polyurethane resin, which is a hardened resin of an adhesive for an endoscope, and
wherein the adhesive for an endoscope contains an ester-based urethane polymer having a structure represented by the following Formula (1):

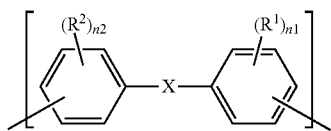

Formula (1)

wherein $R^1$ and $R^2$ each independently represent an alkyl group, an alkoxy group, an alkylthio group, an aryl group, or a halogen atom; n1 and n2 each independently represent an integer of 0 to 4; X represents —C($R^a$)($R^b$)—, —O—, —S—, —SO$_2$—, —C(=O)—, or —N($R^c$)—; $R^a$ and $R^b$ each independently represent a hydrogen atom, an alkyl group, or an aryl group; $R^c$ represents a hydrogen atom or an alkyl group; and $R^a$ and $R^b$ may be bonded to each other to form a ring.

[2] The flexible tube for an endoscope described in the above item [1],
wherein the ester-based polyurethane resin has a polyester structure, in which a diol compound and a dicarboxylic acid compound is being polymerized by condensation polymerization.

[3] The flexible tube for an endoscope described in the above item [1],
wherein the ester-based polyurethane resin has a polyester structure, which is prepared by ring-opening polymerization of a cyclic ester compound.

[4] The flexible tube for an endoscope described in any one of the above items [1] to [3],
wherein an equivalent ratio of an urethane segment with respect to a total of an urethane segment equivalent and an ester segment equivalent in the ester-based urethane polymer is at least 5% and less than 50%.

[5] The flexible tube for an endoscope described in any one of the above items [1] to [4],
wherein an equivalent ratio of an urethane segment with respect to a total of an urethane segment equivalent and an ester segment equivalent in the ester-based polyurethane resin is 5% or more and less than 50%.

[6] The flexible tube for an endoscope described in any one of the above items [1] to [5],
wherein the ester-based polyurethane resin has a shore A hardness according to JIS K7215 of 70 or more and less than 100.

[7] The flexible tube for an endoscope described in any one of the above items [1] to [6],
wherein the ester-based polyurethane resin is a resin, in which the ester-based urethane polymer is hardened with a polyisocyanate compound having at least two isocyanate groups in one molecule thereof.

[8] The flexible tube for an endoscope described in any one of the above items [1] to [7],
wherein the ester-based urethane polymer has a mass average molecular weight of 50,000 or more and 500,000 or less.

[9] The flexible tube for an endoscope described in any one of the above items [1] to [8],
wherein a surface material of the flexible tube substrate material is a stainless steel and/or an aramid fiber.

[10] The flexible tube for an endoscope described in any one of the above items [1] to [9],
wherein the resin layer is composed of a single layer or plural layers, and at least the resin layer, which contacts with the flexible tube substrate material, contains a polyurethane elastomer.

[11] The flexible tube for an endoscope described in any one of the above items [1] to [10],
wherein the resin layer is composed of an inner layer and an outer layer and a thickness ratio of the inner layer and the outer layer varies slopewise in an axial direction of the flexible tube substrate material.

[12] The flexible tube for an endoscope described in the above item [11],
wherein the thickness ratio of the inner layer and the outer layer is from 5:95 to 40:60 at one end of the flexible tube for an endoscope,
wherein the thickness ratio of the inner layer and the outer layer is from 95:5 to 60:40 at the other end of the flexible tube for an endoscope, and
wherein the thickness ratio is turned between both ends.

[13] The flexible tube for an endoscope described in any one of the above items [1] to [12],
wherein the flexible tube for an endoscope is used for an endoscope-type medical device.

[14] An endoscope-type medical device, comprising the flexible tube for an endoscope described in any one of the above items [1] to [13].

[15] An adhesive for an endoscope for adhering a resin layer covering a flexible tube substrate material, comprising an ester-based urethane polymer having a structure represented by the following Formula (1) and a hardener:

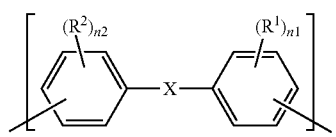

Formula (1)

wherein $R^1$ and $R^2$ each independently represent an alkyl group, an alkoxy group, an alkylthio group, an aryl group, or a halogen atom; n1 and n2 each independently represent an integer of 0 to 4; X represents —C($R^a$)($R^b$)—, —O—, —S—, —SO$_2$—, —C(=O)—, or —N($R^c$)—; $R^a$ and $R^b$ each independently represent a hydrogen atom, an alkyl group, or an aryl group; $R^c$ represents a hydrogen atom or an alkyl group; and $R^a$ and $R^b$ may be bonded to each other to form a ring.

[16] The adhesive for an endoscope described in the above item [15], wherein the hardener is a polyisocyanate compound having at least two isocyanate groups in one molecule thereof.

[17] A method of producing a flexible tube for an endoscope, comprising the steps of:

preparing a flexible tube substrate material;

applying the adhesive for an endoscope described in the above item [15] or [16] to the surface of the flexible tube substrate material; and covering the flexible tube substrate material to which the adhesive for an endoscope is being applied, with a resin layer.

[18] The method of producing a flexible tube for an endoscope described in the above item [17], wherein the resin layer comprises a polyurethane elastomer.

[19] A method of producing an endoscope-type medical device, wherein the endoscope-type medical device is produced through the method of producing a flexible tube for an endoscope described in the above item [17] or [18].

Advantageous Effects of Invention

The flexible tube for an endoscope of the present invention is covered with a resin layer and exhibits high chemical resistance and high peel strength, and also is excellent in both resilient property and flexibility. Further, the endoscope-type medical device of the present invention provided with the flexible tube for an endoscope of the present invention has excellent operability which is suitable for a clinical examination by a doctor as well as reliability and durability due to the various properties of the flexible tube for an endoscope.

Further, by using the adhesive for an endoscope of the present invention, thermal stability at the time of molding is improved, and by the method of producing a flexible tube for an endoscope and the method of producing an endoscope-type medical device according to the present invention, the flexible tube and the endoscope-type medical device both having the above-described excellent performance can be favorably produced.

Other and further features and advantages of the invention will appear more fully from the following description, appropriately referring to the accompanying drawings.

DETAILED DESCRIPTION OF THE INVENTION

Figure 1:
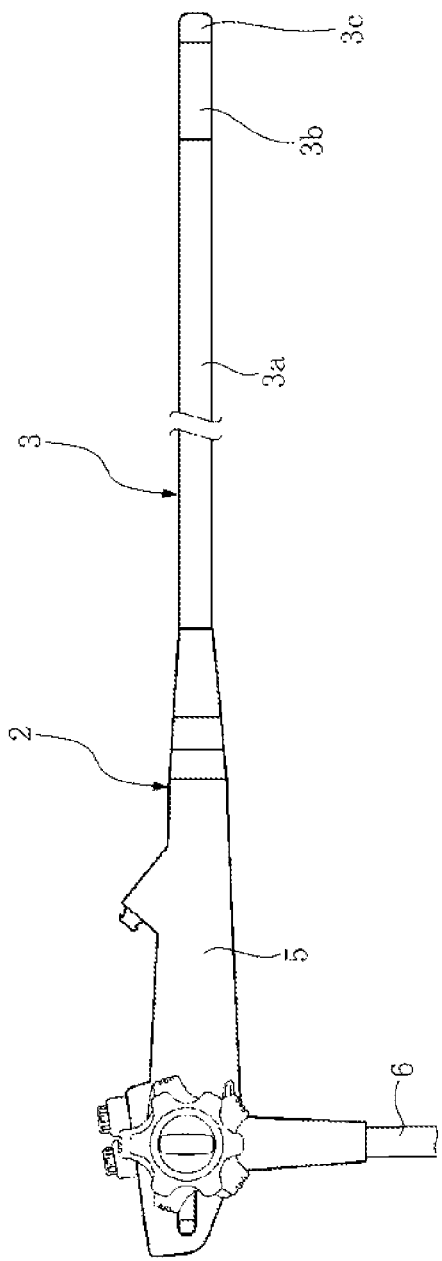
FIG. 1 is an external view showing a configuration of an electronic endoscope.

For the electronic endoscope according to a preferable embodiment of the present invention, a flexible tube is incorporated therein. This sort of product is widely used for medical purposes. In the example shown in FIG. 1, an electronic endoscope 2 contains an insertion unit 3 that is inserted into a body cavity, a main body operating unit 5 provided in conjunction with the base end portion of the insertion unit 3, and a universal code 6 that is connected to a processor device or a light source device. The insertion portion 3 is composed of a flexible tube 3a provided in conjunction with the main body operation portion 5, an angle portion 3b provided in conjunction with the flexible tube 3a, and a tip portion 3c provided in conjunction with a head of the angle portion 3b and being containing an image sensing device (not shown) for photographing a body cavity. The flexible tube 3a which accounts for the majority of the length of the insertion unit 3 has flexibility for much of the entire length thereof. In particular, the site to be inserted into the inside of the body cavity and the like has a structure which has a much flexibility.

(Flexible tube)

Figure 2:
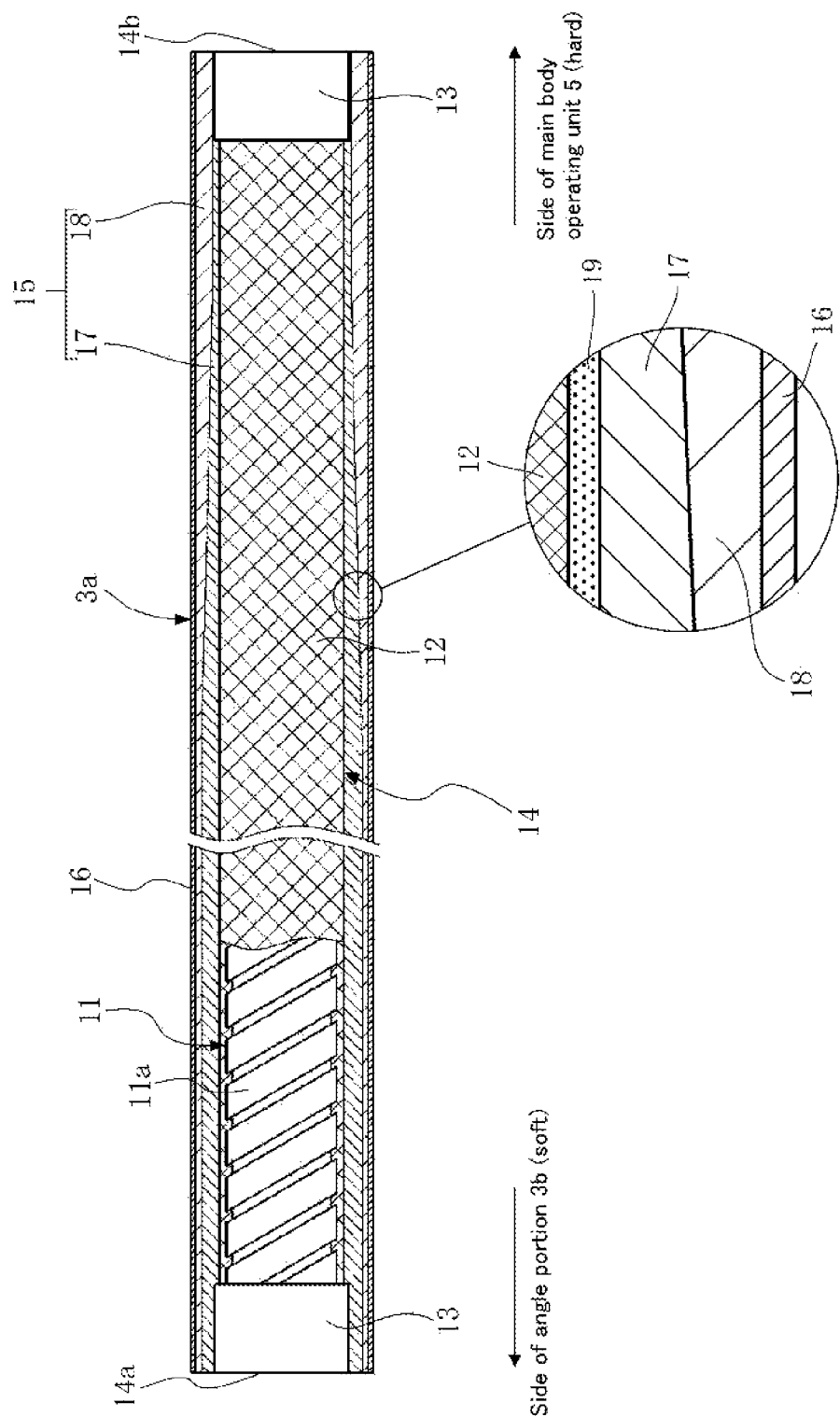
FIG. 2 is a partial cross-section view showing a schematic configuration of a flexible tube.

In the present embodiment, as shown in FIG. 2, the flexible tube 3a (a flexible tube for an endoscope) has a configuration in which a resin layer 15 is coated on an outer peripheral surface of a flexible tube substrate material 14. The flexible tube substrate material 14 has a spiral tube 11 which is formed by winding spirally a metal strip 11a at the innermost side and the spiral tube 11 is covered with a tubular mesh body 12 which is formed by braiding a metal wire. At both ends thereof, caps 13 are each fitted. This resin layer 15 is adhered to the flexible tube substrate material 14 via a layer of an adhesive hardened 19. The layer of an adhesive hardened 19 is shown as a layer having a uniform thickness for convenience in diagrammatic representation. However, the form thereof is not always uniform, but in an indetermination form, the hardened material layer 19 may lie between the resin layer 15 and the flexible tube substrate material 14. Instead, it is preferable that the layer of an adhesive hardened 19 has almost no thickness, and the resin layer 15 and the flexible tube substrate material 14 are mutually adhered substantially in contact with each other.

On an outer surface of the resin layer 15, a coat layer 16 having a chemical resistance and containing, for example, fluorine or the like is coated. The spiral tube 11, although only one single layer is shown, may be constituted in concentrically double layer-superimposed form. The layer of an adhesive hardened 19, the resin layer 15 and the coat layer 16 are drawn thickly with comparison with the size of the flexible tube substrate material 14 in order to show definitely a layer structure.

The resin layer 15 according to the present embodiment covers an outer periphery of the flexible tube substrate material 14. The resin layer 15 has a double layered structure in which an inner layer 17 that covers an entire circumferential surface of the flexible tube substrate material 14 and an outer layer 18 that covers an entire circumferential surface of the inner layer 17 are laminated. A soft resin is used for a material of the inner layer 17, while a rigid resin is used for a material of the outer layer 18.

In the present embodiment, the resin layer 15 is formed in an almost uniform thickness in a longitudinal direction (axial direction) of the flexible tube substrate material 14. The thickness of the resin layer 15 is, for example, from 0.2 mm to 1 mm. The outside diameter D of the flexible tube 3a is, for example, from 10 to 14 mm. The thicknesses of the inner layer 17 and the outer layer 18 are preferably set in such a way that a thickness ratio of the layer 17 and the layer 18 varies slopewise with respect to an entire thickness of the resin layer 15 in an axial direction of the flexible tube substrate material 14. Specifically, in one end 14a side (tip side) of the flexible tube substrate material 14, which is fixed to an angle portion 3b, the thickness of the inner layer 17 is larger than that of the outer layer 18 with respect to an entire thickness of the resin layer 15. Further, toward the other end 14b side (rear anchor side) fitted on the main body operation portion 5 from the one end 14a, the thickness of the inner layer 17 gradually decreases and in the other end 14b side, the thickness of the outer layer 18 is larger than that of the inner layer 17.

In the both ends 14a and 14b of the present embodiment, a thickness ratio of the inner layer 17 and the outer layer 18 is largest. The ratio of the inner layer 17 and the outer layer 18 is 9:1 in the one end 14a and the ratio of the inner layer 17 and the outer layer 18 is 1:9 in the other end 14b. The thickness ratio of the inner layer 17 and the outer layer 18 is reversely altered between both ends 14a and 14b. This causes a difference in hardness between the end 14a and the other end 14b of the flexible tube 3a and thereby flexibility varies in an axial direction in such a way that the one end 14a is flexible and the other end 14b is rigid. Further, it is preferable that the thickness ratio of the above inner layer 17 and outer layer 18 in the one end is from 5:95 to 40:60 (inner layer:outer layer), while the thickness ratio in the other end is in the range of from 95:5 to 60:40 (inner layer:outer layer).

It is preferable to control the thickness ratio of the above inner layer 17 and outer layer 18 in the range of from 5:95 to 95:5 as in the above example. By control of the thickness ratio in this range, the extrusion output of the resin for a thinner layer also can be more precisely controlled.

In terms of 100% modulus value as an index which represents hardness after molding, a difference between a soft resin and a rigid resin which are used for the inner layer 17 and the outer layer 18 is preferably at least 1 MPa, and more preferably at least 3 MPa. A difference between these resins is preferably 2500 Pa·s or less in terms of melt viscosity at a molding temperature of 150° C. to 300° C. as an index which represents fluidity of the resin at a molten state. This enables the resin layer 15 which is composed of the inner layer 17 and the outer layer 18 to obtain both good molding accuracy and a hardness difference required for the tip side 14a and the rear anchor side 14b.

(Method of Producing Flexible Tube)

The method of producing a flexible tube for an endoscope of the present invention contains a step of preparing a flexible tube substrate material, a step of applying an adhesive for an endoscope onto the surface of the flexible tube substrate material, and a step of covering the flexible tube substrate material to which the adhesive for an endoscope has been applied, with a resin layer.

Hereinafter, explanation is given about one example of methods of producing a flexible tube having a double layered structure in which a resin layer is composed of an inner layer and an outer layer. However, other embodiments in which the resin layer is composed of a single layer or at least three layers can be produced in accordance with the following method.

In forming a resin layer which is composed of at least two layers including an inner layer and an outer layer, the following process is preferred:
(i) to prepare a first resin material which constitutes the above inner layer; and on the other hand,
(ii) to prepare a second resin material which constitutes the above outer layer; and
(iii) to extrude and mold the above first resin material and the above second resin material through melting and kneading, on a periphery of the above flexible tube substrate material thereby covering the flexible tube substrate material with the above resin layer.

Figure 3:
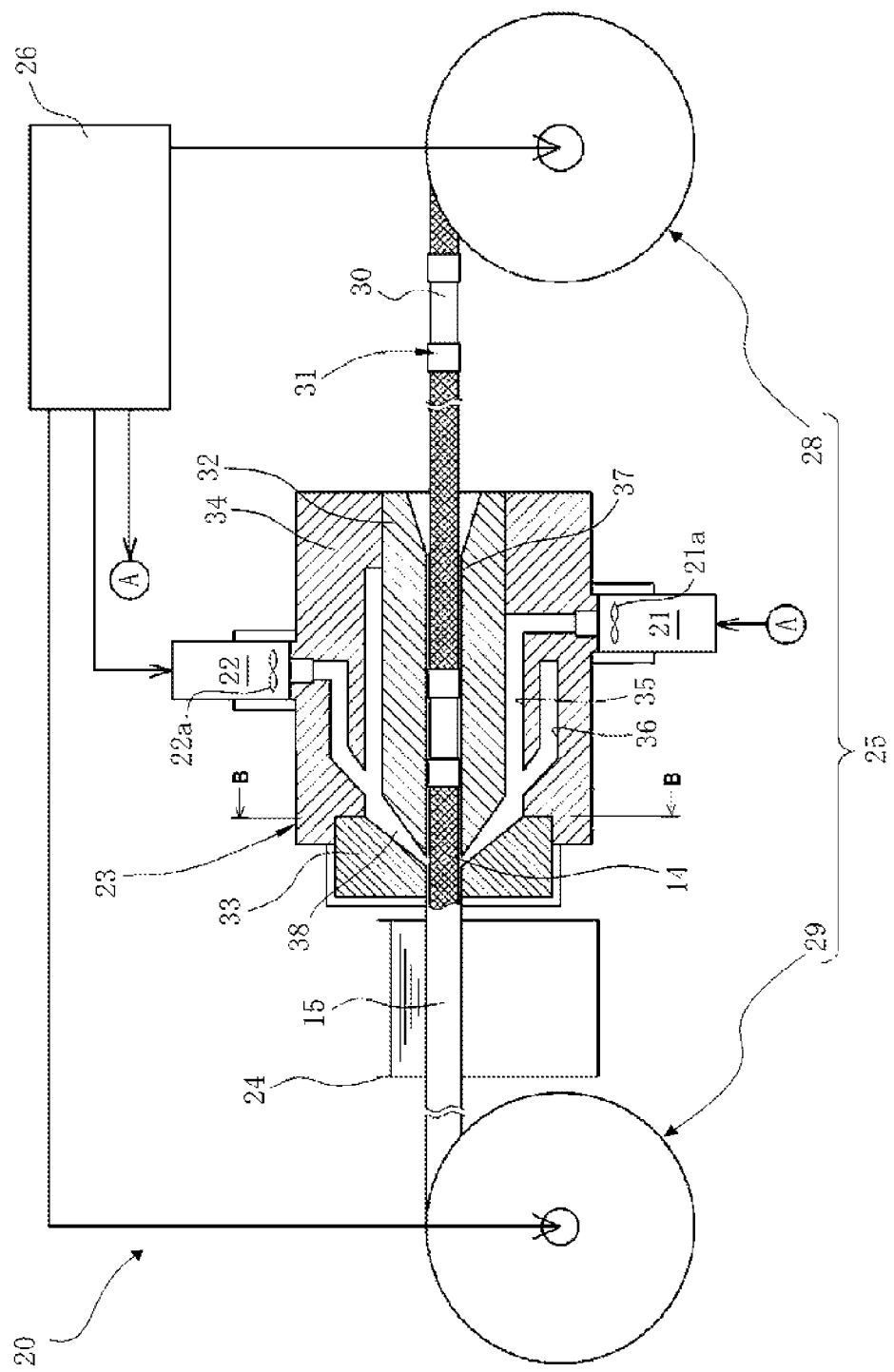
FIG. 3 is a block view schematically showing a configuration of a production equipment of a flexible tube for an endoscope.
Figure 4:
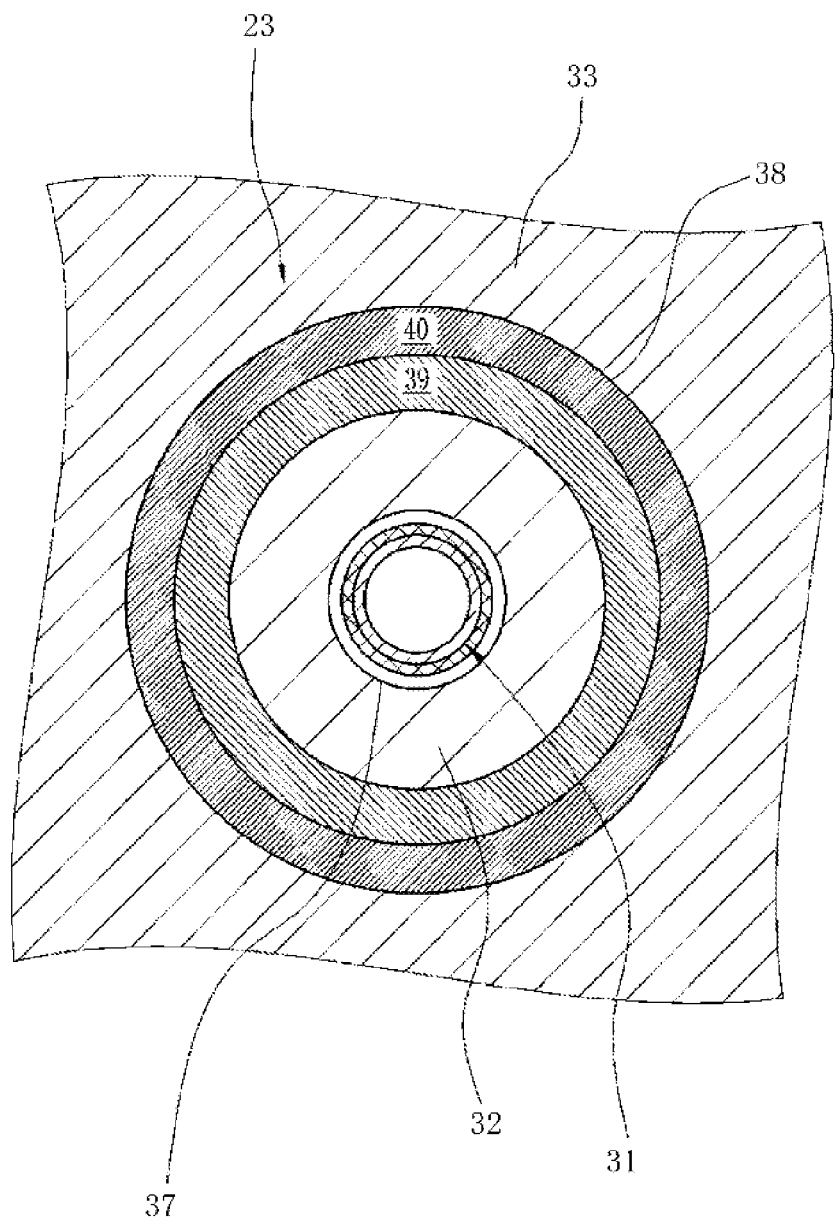
FIG. 4 is a cross-section view cut along the B-B line in FIG. 3.
Figure 5:
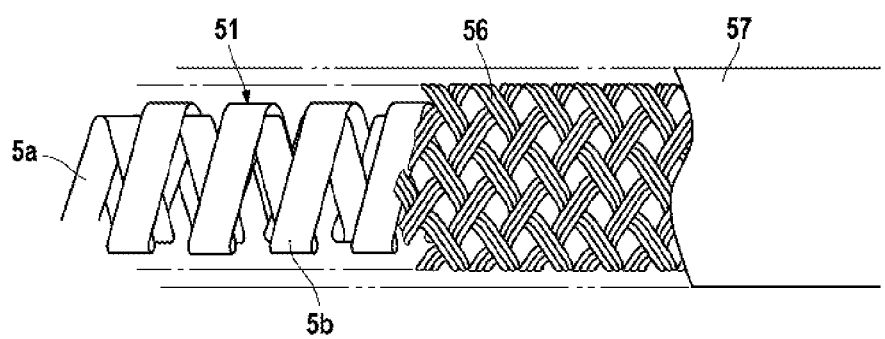
FIG. 5 is a partial cutaway side view for explaining a configuration of the flexible tube used in Examples.

A method of producing a flexible tube 3a (FIG. 1 and FIG. 2) is described on a basis of FIG. 3 and FIG. 4. In this method, use of a continuous molding machine 20 is preferable in order to form a resin layer 15 thereof. The continuous molding machine 20 is preferably used, which machine is composed of: well-known extrusion sections 21 and 22 each composed of a hopper, screws 21a and 22a, and the like; a head section 23 for coating and molding a resin layer 15 on an outer circumferential surface of the flexible tube substrate material 14; a cooling section 24; a conveying section 25 (feeding drum 28 and winding-up drum 29) for conveying a connected flexible tube substrate 31 to the head section 23; and a controlling section 26 for controlling these sections. The head section 23 is preferably composed of a nipple 32, a dies 33, and a support 34 for supporting these components so as to fix them. As an example of the foregoing devices, for example, devices described in FIGS. 3 to 5 of JP-A-2011-72391 may be used. A in FIG. 3 shows that the extrusion section 21 is controlled by the controlling section 26.

The inside of a dies 33 is preferably heated at a predetermined molding temperature. The molding temperature is preferably set to a range of from 150° C. to 300° C. By heating and thermally regulating a heat section in the device, each temperature of the soft resin 39 and the rigid resin 40 can be increased to a higher level. In addition, the higher the rotation frequency of each of the screws 21a and 22a, the higher the each temperature of the soft resin 39 and the rigid resin 40 can be further made, and thereby fluidity of each of these resins can be increased. Further, by keeping a conveying speed of the connected flexible tube 31 constant, and altering each ejecting amount of the soft resin 39 and the rigid resin 40 in the molten state, each of mold thicknesses of the inner layer 17 and the outer layer 18 can be adjusted.

Explanation is given about a process for forming a resin layer 15 on a connected flexible tube substrate material 31 using the continuous molding machine 20. When a molding step is carried out using the continuous molding machine 20, the soft resin 39 and the rigid resin 40 in the molten state are extruded from extrusion sections 21 and 22 to the head section 23. With this, by operation of the conveying section 25, the connected flexible tube substrate material 31 is conveyed to the head section 23. At the time of conveying, the extrusion sections 21 and 22 are in a state of extruding constantly the soft resin 39 and the rigid resin 40 thereby feeding them to the head section 23. The soft resin 39 and the rigid resin 40 which have been extruded from the extrusion sections 21 and 22 to gates 35 and 36, join together through an edge, and are fed to a mold pathway 37 through a resin pathway 38 in a superimposed state. By this process, a two-layered resin layer 15, in which an inner layer 17 using the soft resin 39 and an outer layer 18 using the rigid resin 40 are superimposed, is formed.

At this time, a layer of an adhesive hardened 19 is formed before a flexible tube substrate material 14 is introduced into the mold pathway 37. Specifically, the layer of an adhesive hardened 19 is formed in a manner, in which an adhesive (for example, urethane polymer and polyisocyanate are contained therein) diluted with an organic solvent is coated uniformly on the flexible tube substrate material 14 in a solution state so that the film thickness after drying becomes suitable, and then the organic solvent is dried by heat or the like.

The connected flexible tube substrate material 31 is an article in which a plurality of flexible tube substrate materials 14 are connected to one another, and during conveyance in the mold pathway 37, a resin layer 15 is continuously formed with respect to the plurality of flexible tube substrate materials 14. When the resin layer 15 is formed from one end 14*a* side (tip side) up to the other end 14*b* (rear anchor side) with respect to one flexible tube substrate material 14, the thickness of the inner layer 17 is designed so as to be thicker immediately after the beginning of discharge of the resin by means of the extrusion sections 21 and 22. Then, the thickness ratio of the outer layer 18 is designed so as to be gradually increased at an intermediate portion toward the other end 14*b* side. The discharge amount of the resin is preferably controlled so that the proportion of the thickness in a axis direction of the resin layer 15 becomes slopewise by this process.

A joint member 30 is a joining section of the two flexible tube substrate materials 14 and therefore the controlling section 26 is used to switch a discharge amount of the extrusion sections 21 and 22. Specifically, the controlling section 26 preferably switches a discharge amount of the extrusion sections 21 and 22 so as to become from a thickness ratio at the other end side 14*b* (rear anchor side) of one flexible tube substrate material 14 to a thickness ratio at the one end side 14*a* (tip side) of next flexible tube substrate material 14. When a resin layer 15 is formed from the one end side 14*a* of next flexible tube substrate material 14 up to the other end 14*b* side, the discharge amount of the extrusion sections 21 and 22 are preferably controlled so that the thickness of the outer layer 18 becomes gradually larger toward the other end side from the one end side in the same manner as the above.

The connected flexible tube substrate material 31 on which the resin layer 15 has been coated up to the rear most end is dismounted from the continuous molding machine 20. After that, the joint member 30 is detached from the flexible tube substrate material 14. As a result, the connected flexible tube substrate material is separated into an individual flexible tube substrate material 14. Next, a coat layer 16 is coated on the resin layer 15 with respect to the separated flexible tube substrate material 14. After that, a cap 13 is fitted at both ends whereby a flexible tube 3*a* is completed. The completed flexible tube 3*a* is conveyed to an assembling step of the electronic endoscope 2.

(Flexible Tube Substrate Material [Metal Mesh Tube])

The flexible tube substrate material used in the present invention has a flexibility and a tubular structure. A material of the flexible tube substrate material (metal mesh tube) to be targeted for adhesion is not particularly limited, but it is possible to use appropriately a metallic or aramid fiber, a glass fiber, a carbon fiber and the like, which is used for this kind of products.

As for the metal, for example, copper, a copper alloy, a stainless steel, a nickel titanium alloy, a cobalt chromium-based alloy, pure titanium, a titanium alloy, and a magnesium alloy can be adopted. Among them, from the viewpoints that strength, a resilient property and flexibility of the flexible tube for an endoscope of the present invention is adequately high, and strength of adhesion to a resin layer is adequately high and the flexible tube is excellent in durability, a stainless and/or aramid fiber is preferred for the material of the flexible tube substrate material. In particular, it is preferable that the material of the surface of the flexible tube substrate material is a stainless and/or aramid fiber. In a case where the material surface of the flexible tube substrate material has a reactive polar group (hydroxyl group, carboxylic group, amino group), reactivity with a hardener (for example, isocyanate-based hardener) is high, so that high adhesion strength after curing can be exhibited.

Typically, examples of the tubular mesh body 12 shown in FIG. 2 include braided stainless fibers, braided stainless/aramid fibers, braided aramid fibers and the like. Examples of the metal strip 11*a* being present inside include those made of the above metals and a stainless-steel material may be exemplified.

(Adhesive for Endoscope)

The adhesive hardened used in the present invention contains an ester-based polyurethane resin which is formed by hardening an adhesive for an endoscope. The adhesive for an endoscope contains an ester-based urethane polymer having a structure represented by Formula (1) described below. That is, the ester-based polyurethane resin in the present invention also has a structure represented by Formula (1) described below.

Herein, the ester-based urethane polymer means a urethane polymer having an ester bond in its polymer. Also, the ester-based polyurethane resin means, in the same way, a polyurethane resin having an ester bond in its resin.

The ester-based urethane polymer and the ester-based polyurethane resin used in the present invention are only necessary to contain at least an ester bond, and may contain a repeating unit having other bond such as an ether bond and the like.

In the present invention, a repeating unit, which does not have a urethane bond but has an ester bond, and a repeating unit, which does not have an ester bond but has a urethane bond, may be connected through any repeating structure of random, block, graft, or alternate.

In the present specification, the term "adhesive" means a material having an adhesion function to a member in an uncured state. Typically, the adhesive in a liquid form becomes hardened on a member surface or between members thereby achieving a member-interfacial adhesion.

Further, the term "adhesive hardened" means a member after the adhesive has become hardened. However, the hardened material of an adhesive usually has an indefinite shape, and may be present in the form of a layer between members, or may penetrate into a member to become hardened. Alternatively, the hardened material of an adhesive may be integrated with a part of the member through a reaction therewith.

The layer of an adhesive hardened 19 shown in FIG. 2 is a layer containing the adhesive hardened. However, the layer of an adhesive hardened in the present invention is not construed as being limited to a layer having a uniform layer structure as shown in FIG. 2.

Firstly, explanation is given about a structure represented by the following Formula (1) which the ester-based polyurethane resin and the ester-based urethane polymer in the present invention have.

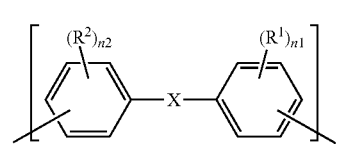

Formula (1)

In Formula (1), $R^1$ and $R^2$ each independently represent an alkyl group, an alkoxy group, an alkylthio group, an aryl group, or a halogen atom; $n1$ and $n2$ each independently represent an integer of 0 to 4; X represents —C($R^a$)($R^b$)—, —O—, —S—, —SO$_2$—, —C(=O)—, or —N($R^c$)—. Herein, $R^a$ and $R^b$ each independently represent a hydrogen atom, an alkyl group, or an aryl group; $R^c$ represents a hydrogen atom or an alkyl group. $R^a$ and $R^b$ may be bonded to each other to form a ring.

The number of carbon atoms of the alkyl group represented by $R^1$ and $R^2$ is preferably 1 to 6, more preferably 1 to 3, further preferably 1 or 2, and particularly preferably 1. Examples of the alkyl group include methyl, ethyl, isopropyl, t-butyl, t-pentyl, and n-hexyl.

The number of carbon atoms of the alkoxy group represented by $R^1$ and $R^2$ is preferably 1 to 6, more preferably 1 to 3, further preferably 1 or 2, and particularly preferably 1. Examples of the alkoxy group include methoxy, ethoxy, isopropyloxy, n-butoxy, isopentyloxy, and n-hexyloxy.

The number of carbon atoms of the alkylthio group represented by $R^1$ and $R^2$ is preferably 1 to 6, more preferably 1 to 3, further preferably 1 or 2, and particularly preferably 1. Examples of the alkylthio group include methylthio, ethylthio, isopropylthio, n-butylthio, isopentylthio, and n-hexylthio.

The number of carbon atoms of the aryl group represented by $R^1$ and $R^2$ is preferably 6 to 20, more preferably 6 to 12, and further preferably 6. Examples of the aryl group include phenyl and naphthyl.

The aryl group may be substituted with an alkyl group (e.g., an alkyl group having preferably 1 to 6 carbon atoms, more preferably 1 to 3 carbon atoms, further preferably 1 or 2 carbon atoms, and particularly preferably 1 carbon atom), an alkoxy group (e.g., an alkoxy group having preferably 1 to 6 carbon atoms, more preferably 1 to 3 carbon atoms, further preferably 1 or 2 carbon atoms, and particularly preferably 1 carbon atom) or a halogen atom.

Examples of the halogen atom include a fluorine atom, a chlorine atom and a bromine atom. Among these, a fluorine atom and a chlorine atom are preferred.

n1 and n2 each independently are preferably an integer of 0 to 2, more preferably 0 or 1, and further preferably 0.

X is preferably —C($R^a$)($R^b$)—, —O—, —S—, —SO$_2$—, or —C(=O)—; more preferably —C($R^a$)($R^b$)—, —S—, or —SO$_2$—; and further preferably —C($R^a$)($R^b$)—.

$R^a$ and $R^b$ each independently are preferably a hydrogen atom or an alkyl group, more preferably a hydrogen atom.

The alkyl group may be substituted with a halogen atom (e.g., a fluorine atom, a chlorine atom, and a bromine atom). Preferred examples of the alkyl group substituted with a halogen atom include trifluoromethyl.

$R^c$ is preferably an alkyl group.

The alkyl group in $R^a$, $R^b$ and $R^c$ has the same meaning as that of the alkyl group in $R^1$ and $R^2$ and the preferable range thereof is also the same.

The aryl group in $R^a$ and $R^b$ has the same meaning as that of the aryl group in $R^1$ and $R^2$ and the preferable range thereof is also the same.

The ring which is formed by a mutual combination of $R^a$ and $R^b$ is preferably a 5- or 6-membered ring, more preferably a cyclopentane ring or a cyclohexane ring, and still more preferably a cyclohexane ring.

Specific examples of X include —CH$_2$—, —CH(CH$_3$)—, —C(CH$_3$)$_2$—, —CH(i-C$_3$H$_7$)—, —C(CF$_3$)$_2$—, —CH(C$_6$H$_5$)—, —O—, —S—, —SO$_2$—, —N(CH$_3$)—, cyclopentylidene, and cyclohexylidene. Among these, —CH$_2$—, —CH(CH$_3$)—, —C(CH$_3$)$_2$—, and —C(CF$_3$)$_2$— are preferred; —CH$_2$—, —CH(CH$_3$)—, and —C(CH$_3$)$_2$— are more preferred; and —CH$_2$— is further preferred.

As the structure represented by Formula (1), a structure in which n1 and n2 are 0, and X is —CH$_2$—, is most preferred.

The structure represented by the Formula (1) is only necessary to be present in the ester-based polyurethane resin. In other words, any of the raw materials which form an ester bond and a urethane bond as described below are only necessary to have the structure represented by the Formula (1).

In the present invention, above all, the structure represented by the Formula (1) is preferably incorporated in the ester-based polyurethane resin in the form of —OC(=O)NH-[a group of the structure represented by the Formula (1)]-NHC(=O)O—.

The structure represented by Formula (1) is more preferably a structure represented by Formula (2).

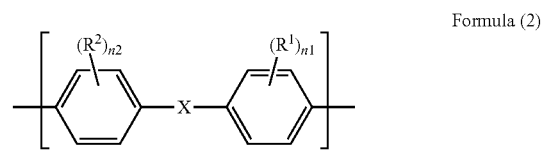

Formula (2)

In Formula (2), $R^1$, $R^2$, n1, n2 and X each have the same meaning as $R^1$, $R^2$, n1, n2 and X in Formula (1); and preferable ranges thereof are also the same.

As the structure represented by Formula (2), a structure, in which n1 and n2 are 0 and X is a methylene group, is most preferred.

(Adhesive for Endoscope)

The adhesive for an endoscope of the present invention (hereinafter, also referred to simply as an adhesive) contains an ester-based urethane polymer having a structure represented by the Formula (1), and a hardener.

It is supposed that by the adhesive for an endoscope of the present invention, resistance to an extraneous physical stimulus exerts due to a stereoscopic specificity which the structure represented by the Formula (1) has, so that the flexible tube for an endoscope of the present invention (hereinafter, also referred to simply as a flexible tube) exhibits a high resilient property.

Further, it is presumed that due to hydrophobic properties and steric hindrance which the structure represented by the Formula (1) has, the flexible tube for an endoscope of the present invention becomes less affected by attack from chemicals such as a disinfectant or the like whereby disinfectant resistance or chemical resistance can be enhanced.

Specifically, it is presumed that a urethane bond which the ester-based urethane polymer has, or a urethane bond or an allophanate bond which is formed by a reaction with a polyisocyanate hardener is protected from an aqueous chemical liquid such as a disinfectant.

The adhesive of the present invention is preferably used for adhesion of a flexible tube substrate material and a resin layer covering the flexible tube substrate material. This adhesive can be widely used for adhesion in other intended purpose. In this case, application to adhesion of different materials between a metal or resin material and a urethane elastomer is preferable. A preferable range of the metal and resin material to be an adhesion target is the same as the above-described preferable range of the flexible tube substrate material.

Ester-Based Urethane Polymer

The ester-based urethane polymer in the present invention is a polymer having an ester bond and a urethane bond in the structure thereof.

Hereinafter, the ester-based urethane polymer is explained in more detail by describing raw materials for forming an ester bond or a urethane bond.

i) Ester Bond

The ester bond is formed by, for example, condensation polymerization of a polybasic carboxylic acid compound and a compound having at least two hydroxyl groups in one molecule, or a ring-open polymerization of a cyclic ester compound.

Of the polybasic carboxylic acid compounds, a dicarboxylic acid compound is preferable. Examples thereof include an aliphatic saturated dicarboxylic acid, an aliphatic unsaturated dicarboxylic acid, a carbocyclic dicarboxylic acid, and an aromatic dicarboxylic acid. In the present invention, however, a dicarboxylic acid having an acyclic structure is not preferable.

The number of carbon atoms of the dicarboxylic acid compound is preferably 2 to 14, more preferably 4 to 10, and further preferably 4 to 6.

Examples of the dicarboxylic acid compound include malonic acid, succinic acid, glutaric acid, adipic acid, pimelic acid, suberic acid, azelaic acid, sebacic acid, maleic acid, fumaric acid, citraconic acid, mesaconic acid, cyclohexane-1,2-dicarboxylic acid, cyclohexane-1,3-dicarboxylic acid, cyclohexane-1,4-dicarboxylic acid, phthalic acid, isophthalicacid, terephthalicacid, naphthalene-2,3-dicarboxylic acid, naphthalene-1,4-dicarboxylic acid, naphthalene-2,6-dicarboxylic acid, bis(4-carboxyphenyl)methane, and 2,2-bis(4-carboxyphenyl)hexafluoropropane.

In the present invention, an aliphatic saturated dicarboxylic acid is preferable. The number of carbon atoms is preferably 4 to 6. Specific preferred examples thereof include succinic acid, glutaric acid, and adipic acid.

Examples of the compound having at least two hydroxyl groups in one molecule include a diol compound, a glycol compound (a compound having two hydroxyl groups in one molecule, for example, an aliphatic glycol, an alicyclic glycol), and a polyol (a compound having at least three hydroxyl groups in one molecule, for example, a polyether polyol compound, a polyester polyol compound, a polymer polyol compound). In the present invention, however, a compound having an acyclic structure and at least two hydroxyl groups in one molecule is not preferable.

Specific examples of the diol compound, the glycol and the polyether polyol compound, of the compound having at least two hydroxyl groups in one molecule, include ethylene glycol, diethylene glycol, propylene glycol, dipropylene glycol, 1,4-butanediol, 1,5-pentanediol, 1,6-hexanediol, neopentylglycol, 1,2-cyclohexanedimethanol, cyclopentane-1,2-diol, glycerin, 1,1,1-trimethylolpropane, 1,2,5-hexanetriol, pentaerythritol, glucose, sorbitol, sucrose, bisphenol A, bisphenol F, bisphenol S, bisphenol AF, brominated bisphenol A, hydrogenated bisphenol A, hydrogenated bisphenol F, an ethylene oxide adduct of bisphenol A, a propylene oxide adduct of bisphenol A, an ethylene oxide adduct of bisphenol F, a propylene oxide adduct of bisphenol F, an ethylene oxide adduct of hydrogenated bisphenol A, and a propylene oxide adduct of hydrogenated bisphenol A.

Examples of the polyester polyol compound include; a condensation polymer of at least one selected from the above-described diol compound, glycol and polyether polyol compound and at least one selected from the above-described polybasic carboxylic acid compounds; and a polymer of at least one selected from the above-described diol compound, glycol and polyether polyol compound and a ring-open polymer of a cyclic ester compound as described below.

Examples of commercial products of the polyester diol compound include POLYLITE series (manufactured by DIC Corporation); Kuraray Polyol P-series, Kuraray Polyol F-series, Kuraray Polyol N-series, and Kuraray Polyol PMNA-series (manufactured by KURARAY CO., LTD.); and PLACCEL series (manufactured by Daicel Corporation) (all trade names).

In the present invention, an aliphatic diol is preferable. The number of carbon atoms is preferably 2 to 12, more preferably 4 to 10, and further preferably 4 to 6. Specific preferred examples thereof include 1,4-butanediol, 1,5-pentanediol, and 1,6-hexanediol.

The number of carbon atoms of the cyclic ester compound is preferably 4 to 12, more preferably 6 to 10, and further preferably 6 to 8. Above all, a compound in which the number of ring-constituting atom is odd is preferable.

Specific examples thereof include γ-butyrolactone, δ-valerolactone, γ-caprolactone, δ-caprolactone, and ε-caprolactone. Among these, γ-butyrolactone, γ-caprolactone and ε-caprolactone are preferred.

The ester bond may be formed by bringing about a reaction between a raw material forming the above ester bond and a raw material forming a urethane bond at the same time in the formation of the urethane bond, or alternatively a compound having an ester bond may be used as a raw material forming a urethane bond.

Examples of the material having an ester bond include the above-described polyester polyol compound.

In the present invention, a polyester bond obtained by a condensation polymerization of a dicarboxylic acid compound and a compound having at least two hydroxyl groups in one molecule (preferably a diol compound) is preferable from the viewpoint of a resilient property.

ii) Urethane Bond

The urethane bond is formed, for example, by a condensation polymerization of a diisocyanate compound and a compound having at least two hydroxyl groups in one molecule.

The diisocyanate compound is more preferably a compound represented by Formula (3).

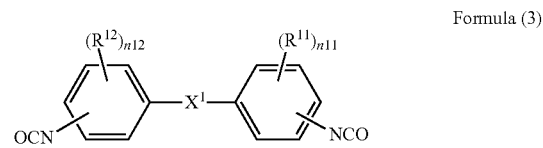

Formula (3)

In Formula (3), $R^{11}$ and $R^{12}$ each independently represent an alkyl group, an alkoxy group, an alkylthio group, an aryl group, or a halogen atom; n11 and n12 each independently represent an integer of 0 to 4; $X^1$ represents —C($R^{1a}$)($R^{1b}$)—, —O—, —S—, —SO$_2$—, —C(=O)—, or —N($R^{1c}$)—. Herein, $R^{1a}$ and $R^{1b}$ each independently represent a hydrogen atom, an alkyl group, or an aryl group; $R^{1c}$ represents a hydrogen atom or an alkyl group. $R^{1a}$ and $R^{1b}$ may be bonded to each other to form a ring.

The number of carbon atoms of the alkyl group represented by $R^{11}$ and $R^{12}$ is preferably 1 to 6, more preferably 1 to 3, further preferably 1 or 2, and particularly preferably 1.

The number of carbon atoms of the alkoxy group represented by $R^{11}$ and $R^{12}$ is preferably 1 to 6, more preferably 1 to 3, further preferably 1 or 2, and particularly preferably 1.

The number of carbon atoms of the alkylthio group represented by $R^{11}$ and $R^{12}$ is preferably 1 to 6, more preferably 1 to 3, further preferably 1 or 2, and particularly preferably 1.

The number of carbon atoms of the aryl group represented by $R^{11}$ and $R^{12}$ is preferably 6 to 12, more preferably 6 to 10, and further preferably 6.

The aryl group may be substituted with an alkyl group (e.g., an alkyl group having preferably 1 to 6 carbon atoms, more preferably 1 to 3 carbon atoms, further preferably 1 or 2 carbon atoms, and particularly preferably 1 carbon atom), an alkoxy group (e.g., an alkoxy group having preferably 1 to 6 carbon atoms, more preferably 1 to 3 carbon atoms, further preferably 1 or 2 carbon atoms, and particularly preferably 1 carbon atom) or a halogen atom.

Examples of the halogen atom include a fluorine atom, a chlorine atom and a bromine atom. Among these, a fluorine atom and a chlorine atom are preferred.

n11 and n12 each independently are preferably an integer of 0 to 2, more preferably 0 or 1, and further preferably 0.

$X^1$ is preferably —C($R^{1a}$)($R^{1b}$)—, —O—, —S—, —SO$_2$—, or —C(=O)—; more preferably —C($R^{1a}$)($R^{1b}$)—, —S—, or —SO$_2$—; and further preferably —C($R^{1a}$)($R^{1b}$)—.

The number of carbon atoms of the alkyl group represented by $R^{1a}$ and $R^{1b}$ is preferably 1 to 6, more preferably 1 to 3, further preferably 1 or 2, and particularly preferably 1.

The number of carbon atoms of the aryl group represented by $R^{1a}$ and $R^{1b}$ is preferably 6 to 12, more preferably 6 to 10, and further preferably 6.

$R^{1a}$ and $R^{1b}$ each independently are preferably a hydrogen atom or an alkyl group, more preferably a hydrogen atom or an alkyl group having 1 to 3 carbon atoms, and further preferably a hydrogen atom.

The alkyl group may be substituted with a halogen atom (e.g., a fluorine atom, a chlorine atom or a bromine atom). Preferred examples of the alkyl group substituted with a halogen atom include trifluoromethyl.

Specific examples of $X^1$ include those exemplified as X, and a preferable range is also the same.

As the structure represented by Formula (3), a structure, in which n11 and n12 are 0 and $X^1$ is a methylene group, is most preferred.

The compound represented by Formula (3) is preferably a compound represented by Formula (4).

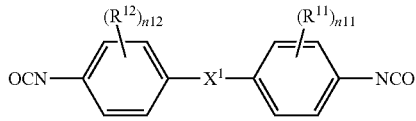

Formula (4)

In Formula (4), $R^{11}$, $R^{12}$, n11, n12 and $X^1$ each have the same meaning as $R^{11}$, $R^{12}$, n11, n12 and $X^1$ in Formula (3); and preferable ranges thereof are also the same.

Examples of the diisocyanate compound include 2,2'-diphenylmethane diisocyanate (2,2'-MDI), 2,4'-diphenylmethane diisocyanate (2,4'-MDI), 4,4'-diphenylmethane diisocyanate (4,4'-MDI), bis(3-methyl-4-isocyanatophenyl)methane, bis(3-ethyl-4-isocyanato-5-methylphenyl)methane, bis(3-chloro-4-isocyanatophenyl)methane, bis(2,3-dichloro-4-isocyanatophenyl)methane, 1,1-bis(4-isocyanatophenyl)cyclohexane, 2,2-bis(4-isocyanatophenyl)hexafluoropropane, N,N-bis(4-isocyanatophenyl)amine, bis(4-isocyanatophenyl)sulfide, bis(4-isocyanatophenyl)sulfone, bis(4-isocyanatophenyl)ether, and 4,4'-diisocyanatobenzophenone.

Among these, 4,4'-diphenylmethane diisocyanate (4,4'-MDI), bis(3-methyl-4-isocyanatophenyl)methane, bis(3-ethyl-4-isocyanato-5-methylphenyl)methane, bis(3-chloro-4-isocyanatophenyl)methane, bis(2,3-dichloro-4-isocyanatophenyl)methane, 2,2-bis(4-isocyanatophenyl)hexafluoropropane, bis(4-isocyanatophenyl)sulfide, and bis(4-isocyanatophenyl)sulfone are preferred; 4,4'-diphenylmethane diisocyanate (4,4'-MDI), bis(3-methyl-4-isocyanatophenyl)methane, bis(3-ethyl-4-isocyanato-5-methylphenyl)methane, bis(3-chloro-4-isocyanatophenyl)methane, bis(2,3-dichloro-4-isocyanatophenyl)methane, and 2,2-bis(4-isocyanatophenyl)hexafluoropropane are more preferred; 4,4'-diphenylmethane diisocyanate (4,4'-MDI), bis(3-methyl-4-isocyanatophenyl)methane, bis(3-chloro-4-isocyanatophenyl)methane, and 2,2-bis(4-isocyanatophenyl)hexafluoropropane are further preferred; and 4,4'-diphenylmethane diisocyanate (4,4'-MDI) is particularly preferred.

Examples of the compound having at least two hydroxyl groups in one molecule include diol, glycol (a compound having two hydroxyl groups in one molecule, for example, aliphatic glycol, alicyclic glycol), and a polyol compound (a compound having at least three hydroxyl groups in one molecule, for example, polyether polyol, polyester polyol, polymer polyol), all of which is described in the above ester bond. The compound having at least two hydroxyl groups in one molecule is the same in a preferable range as these exemplified compounds.

Formation of the ester bond and the urethane bond can be carried out respectively in accordance with a usual method.

An urethane bond-forming reaction can be promoted by use of an organic tin catalyst as a metal catalyst. However, the catalyst does not contain a tertiary amine catalyst having a morpholine skeleton.

Examples of the organic tin catalyst include stannous diacetate, stannous dioctoate, stannous dioleate, dibutyl tin dilaurate, dibutyl tin maleate, and dioctyl tin laurate.

The blend amount of the organic tin catalyst is preferably from 0.001 to 0.50 parts by mass with respect to 100 parts by mas of the compound having at least two hydroxyl groups in one molecule.

In the ester-based urethane polymer in the present invention, the equivalent ratio of a urethane segment (hereinafter, also referred to as a urethane segment ratio) with respect to the total equivalent of the urethane segment and an ester segment is calculated by the following formula.

The urethane segment equivalent ratio means a molar ratio of the urethane segment.

Urethane segment ratio (%)=Urethane segment equivalent/(Urethane segment equivalent+Ester segment equivalent)×100%

The urethane segment ratio is preferably at least 5% and less than 50%, more preferably at least 5% and less than 40%, and still more preferably at least 5% and less than 20%.

In a case where the urethane segment ratio is in a range of from at least 5% to less than 50% is preferable from the view point of superiority in both bending durability and peeling strength.

Herein, the term "urethane segment" represents a polymer of the diisocyanate compound and the compound having at least two hydroxyl groups in one molecule as described above. A substance in which one diisocyanate compound and one compound having at least two hydroxyl groups in one molecule is combined to form one urethane bond is defined as 1 urethane unit.

Further, the term "ester segment" represents a polymer of a dicarboxylic acid compound and a compound having at least two hydroxyl groups in one molecule, and a ring-open polymer of a cyclic ester compound as described above. A substance in which one dicarboxylic acid compound and one compound having at least two hydroxyl groups in one molecule is combined to form one ester bond or a ring-opened substance of one cyclic ester compound is defined as 1 ester unit.

The mass-average molecular weight of the ester-based urethane polymer is preferably at least 50,000, more preferably at least 90,000, and still more preferably at least 120,000. The upper limit thereof is preferably equal to or less than 500,000, more preferably equal to or less than 300,000, and still more preferably equal to or less than 150,000.

By adjusting the mass-average molecular weight of the ester-based urethane polymer to this range, adhesion strength between a flexible tube substrate material and a resin layer can be kept at a high level, and also a viscosity at the time when an adhesive layer is coated on the flexible tube substrate material is good, so that excellent handling property can be preferably obtained.

A reaction of a polyol compound and a polyisocyanate compound can be performed in a usual manner.

A urethane adhesive can be referred to, for example, JP-A-6-234963, JP-A-3-95287, Japanese Patent No. 3114341, Japanese Patent No. 5015098, and the like.

Hardener

The adhesive for an endoscope of the present invention preferably contains a hardener for hardening the ester-based urethane polymer having the structure represented by the Formula (1).

As for the hardener in the present invention, a polyisocyanate compound having at least two isocyanate groups in the molecule thereof (hereinafter also referred to simply as a polyisocyanate compound) is preferred. The number of the isocyanate group in the molecule is more preferably at least 3, and the upper limit thereof is practically equal to or less than 8, and more practically equal to or less than 6.

Examples of the polyisocyanate compound include a straight-chain aliphatic polyisocyanate, an acyclic polyisocyanate and an aromatic polyisocyanate. The polyisocyanate compound may be any of a low molecular compound and a high molecular compound, and may be a simple polyisocyanate, or any other polyisocyanates selected from biuret (dimer) type, isocyanurate (trimer) type, adduct (addition body) type, bifunctional type polyisocyanates and modified ones thereof.

Specifically, examples thereof includes: an aromatic diisocyanate compound such as 2,4-tolylenediisocyanate, a dimer of 2,4-tolylenediisocyanate, a trimer of 1,6-hexamethylenediisocyanate, 2,6-tolylenedilenediisocyanate, p-xylylenediisocyanate, m-xylylenediisocyanate, 4,4'-diphenylmethanediisocyanate (4,4'-MDI), 1,5-naphthylenediisocyanate, and 3,3'-dimethylbiphenyl-4,4'-diisocyanate; an aliphatic diisocyanate compound such as hexamethylenediisocyanate, trimethylhexamethylenediisocyanate, lysinediisocyanate, and dimer acid diisocyanate; an alicyclic diisocyanate such as isophorone diisocyanate, 4,4'-methylene bis(cyclohexylisocyanate), methylcyclohexane-2,4 (or 2,6)-diisocyanate, and 1,3-(isocyanate methyl)cyclohexane; and a reaction product of a polyalcohol and a diisocyanate compound such as an adduct of 1 mole of 1,3-butylene glycol and 2 moles of tolylenediisocyanate, and a trimethylol propane adduct of 2,4-tolylenediisocyanate; and the like. As to these compounds, one kind may be used solely or at least 2 kinds may be used in combination. Among these compounds, 4,4'-diphenylmethane diisocyanate (MDI) is preferred. In the present invention, however, the polyisocyanate compound having an alicyclic structure is not preferred.

Examples of the commercialized product include a trimethylol propane adduct of 2,4-tolylenediisocyanate (trade name "COLONATE L", manufactured by Nippon Urethane Industries Co., Ltd.), a trimer of 1,6-hexamethylenediisocyanate (trade name "DURANATE TPA-100", manufactured by Asahi Kasei Chemicals Corporation), and a trimer modified product of 1,6-hexamethylenediisocyanate (trade name "COLONATE HXLV", manufactured by Nippon Urethane Industries Co., Ltd.).

The blend amount of an ester-based urethane polymer and a hardener in the adhesive for an endoscope is not particularly limited. The amount of the hardener is preferably at least 0.5 parts by mass, more preferably at least 1 part by mass, and still more preferably at least 2 parts by mass, with respect to 100 parts by mass of the ester-based urethane polymer. The upper limit thereof is preferably equal to or less than 25 parts by mass, more preferably equal to or less than 20 parts by mass, and still more preferably equal to or less than 15 parts by mass.

By adjusting the blend ratio of the adhesive component to this range, adhesion strength between a flexible tube substrate material and a resin layer, particularly adhesion strength after a treatment with a disinfectant can be preferably enhanced.

The ester-based urethane polymer which constitutes the adhesive for an endoscope may be used solely without containing a hardener. In this case, it is preferred that the ester-based urethane polymer has an end group (for example, isocyanate group) that acts as a hardener.

In the present invention, by using an adhesive in which the ester-based urethane polymer and the hardener are separately blended as individual compounds, rather than a compound in which an end group in the ester-based urethane polymer also acts as a hardener, better adhesion property and chemical resistance can be preferably obtained.

Solvent

The adhesive may contain solvent. Solvents used are not particularly limited. For example, an organic solvent is exemplified. Specific examples thereof include the following solvents:

Alcohol compound solvent, such as methyl alcohol, ethyl alcohol, 1-propyl alcohol, 2-propyl alcohol, 2-butanol, ethylene glycol, propylene glycol, glycerin, 1,6-hexanediol, cyclohexanediol, sorbitol, xylitol, 2-methyl-2,4-pentanediol, 1,3-butanediol, and 1,4-butanediol;

Ether compound solvent (including an ether compound containing a hydroxyl group), such as dimethyl ether, diethyl ether, diisopropyl ether, dibutyl ether, t-butylmethyl ether, cyclohexylmethyl ether, anisole, tetrahydrofuran, and an alkylene glycol alkyl ether (e.g., ethylene glycol monomethyl ether, ethylene glycol monobutyl ether, diethylene glycol, dipropylene glycol, propylene glycol monomethyl ether, diethylene glycol monomethyl ether, triethylene glycol, polyethylene glycol, propylene glycol monomethyl ether, dipropylene glycol monomethyl ether, tripropylene glycol monomethyl ether, and diethylene glycol monobutyl ether);

Amide compound solvent, such as N,N-dimethylformamide, N-methyl-2-pyrrolidone, 2-pyrrolidinone, 1,3-dimethyl-2-imidazolidinone, ε-caprolactam, formamide, N-methylformamide, acetamide, N-methylacetamide, N,N-dimethylacetamide, N-methylpropanamide, and hexamethylphosphoric triamide;

Ketone compound solvent, such as acetone, methyl ethyl ketone, methyl isobutyl ketone, and cyclohexanone;

Aromatic compound solvent such as benzene and toluene;

Aliphatic compound solvent, such as hexane, heptane, cyclohexane, methylcyclohexane, octane, pentane, and cyclopentane; and Nitrile compound solvent, such as acetonitrile.

As to the above solvent, one kind may be used solely, or at least two kinds may be used in combination.

An amount of the adhesive components (the ester-based urethane polymer and the hardener) with respective to the solvent may be adjusted appropriately. The amount of the adhesive components is preferably at least 1% by mass, more preferably at least 2% by mass, and particularly preferably at least 4% by mass, with respective to the solvent. The upper limit thereof is preferably equal to or less than 30% by mass, more preferably equal to or less than 20% by mass, and still more preferably equal to or less than 15% by mass.

By adjusting the concentration of the adhesive component to the preferable range described above, the thickness of the adhesive layer after coating can be controlled in an appropriate range.

A method of applying an adhesive to a flexible tube substrate material is not particularly limited. The adhesive is preferably coated in a usual manner. A coating amount is not particularly limited. The lower limit thereof is preferably at least 10 g/m$^2$, and the upper limit thereof is preferably equal to or less than 1000 g/m$^2$.

A hardening method of the adhesive is not particularly limited. Examples thereof include a natural hardening method at room temperature, a thermal hardening method, and a hardening method by adding a metal catalyst such as dibutyl tin dilaurate described above. However, the catalyst does not contain a tertiary amine catalyst having a morpholine skeleton.

It is also preferred that, before the above-described hardening treatment, the flexible tube substrate material is preliminarily pretreated by heat as a temporary fixing. The heating temperature for the temporary fixing is preferably at least 50° C., more preferably at least 70° C., and particularly preferably at least 90° C. The upper limit is preferably equal to or less than 180° C., and more preferably equal to or less than 150° C.

Herein, explanation is given about a hardening reaction of the ester-based urethane polymer due to a polyisocyanate compound.

A urethane bond is formed by a reaction of an end-hydroxyl group of the ester-based urethane polymer and an isocyanate group of the polyisocyanate compound whereby hardening is progressed. Further, by a reaction of the urethane bond of the ester-based urethane polymer and the isocyanate group of the polyisocyanate compound, an allophanate bond (cross-link) is formed. By progress of these reactions, an ester-based polyurethane resin that is a cross-linking structure body is formed whereby an adhesion structure of the member is formed.

A shore A hardness based on JIS K7215 of the ester-based polyurethane resin in the present invention is preferably at least 70 and less than 100. The lower limit is more preferably at least 75, and still more preferably at least 80, and the upper limit is more preferably equal to or less than 98, and still more preferably equal to or less than 97.

The peeling strength of a flexible tube, in which the ester-based polyurethane resin in the present invention is contained in the adhesive hardened, is acceptable, if it is at least 15 N/cm, preferably at least 20 N/cm, and more preferably at least 30 N/cm.

The peeling strength in the present specification means a value obtained by measuring of the flexible tube prepared in accordance with the Example described below, in accordance with the peeling test described in the Example.

(Resin Layer)

As for the resin layer used in the present invention, a resin which is usually incorporated in this kind of products can be used appropriately. Examples thereof include a resin selected from a group consisting of a polyester elastomer, a polyurethane elastomer and a polyamide elastomer.

The resin layer may be composed of a single layer or a multiple layers consisting of at least two layers. In the present invention, from the viewpoints of a good compatibility with an adhesive containing an ester-based urethane polymer, so that a good performance can be obtained, the resin layer preferably contains a polyurethane elastomer and at least the resin layer in the side having contact with a flexible tube substrate material more preferably contains a polyurethane elastomer.

In the present invention, the resin layer is preferably composed of a multiple layers, and more preferably composed of two layers consisting of an inner layer and an outer layer. In a case where the resin layer is composed of a multiple layers, the layer having contact with the flexible tube substrate material is referred to as an inner layer and the layer located at the position furthest away from the flexible tube substrate material is referred to as an outer layer.

By a double-layered structure of the resin layer, resins that are appropriate to a role of each of the inner layer and the outer layer of the resin layer can be each used, so that higher product performance can be elicited. In a case where the resin layer is double-layered, a polyurethane elastomer is preferably applied to the inner layer.

In a case where resins are blended to constitute a resin layer, the inner layer and the outer layer are preferably constituted as set forth in the following lists.

| <Outer layer> | |
|---|---|
| Main elastomer | Sub elastomer |
| PE | PU |
| PE | PA |
| PE | PU + PA |
| PU | PE |
| PU | PA |
| PU | |

| <Inner layer> | |
|---|---|
| Main elastomer | Sub elastomer |
| PU | PE |
| PU | PA |
| PU | |

The above abbreviations mean the following elastomers.
PE: Polyester elastomer
PU: Polyurethane elastomer
PA: Polyamide elastomer Explanation is given in more detail about polyurethane elastomers which can be adopted preferably in the present invention. The polyurethane elastomer in the present embodiment can be obtained by reacting a polyisocyanate compound, a polyol compound, and a chain extender, and is preferably a block copolymer which is comprised of a soft segment obtained by a reaction between the polyol compound and the polyisocyanate compound, and a hard segment obtained by a reaction between the chain extender and the polyisocyanate compound.

Examples of the polyisocyanate compound include diphenylmethane diisocyanate, hexamethylenediisocyanate, tolidine diisocyanate, 1,5-naphthalene diisocyanate, isophorone diisocyanate, and xylylene diisocyanate.

Among these, diphenylmethane diisocyanate and/or hexamethylene diisocyanate are preferable from the viewpoint of abrasion resistance of the thermoplastic polyurethane resin, and diphenylmethane diisocyanate is preferable from the viewpoints of chemical resistance and a resilient property.

Examples of the polyol compound include polytetramethylene ether glycol, polyester polyol, and lactone-based polyester polyol. The polyester polyol can be obtained by a polycondensation reaction between a dicarboxylic acid compound and a diol compound. Specific examples of the diol compound which is used for production of the polyester polyol include ethane diol, 1,3-propane diol, 1,4-butane diol, 1,5-pentane diol, 1,6-hexanediol and the like, which are used either alone or in combination. Further, examples of the dicarboxylic acid compound include adipic acid, sebacic acid, and the like, which are used either alone or in combination.

Among these polyol compounds, polytetramethylene ether glycol is preferred from the viewpoint that a thermoplastic polyurethane resin having a high resilient property is obtained by this polyol compound.

Further, examples of the chain extender include: an aliphatic straight-chain diol compound having 2 to 6 carbon atoms such as ethane diol, 1,4-butane diol, and 1,6-hexane diol; 1,4-bis(hydroxyethoxy)benzene, and the like. Amines such as hexamethylenediamine, isophoronediamine, tolylenediamine, monoethanolamine, and the like may be used partially in combination with the chain extender. Among these compounds, an aliphatic straight-chain diol compound having 2 to 6 carbon atoms is preferable from the viewpoints of abrasion resistance of the thermoplastic polyurethane resin.

As to the polyurethane elastomers involved in the above-described embodiment, the disclosure of JP-A-2005-015643 may be referred to.

The content of the polyurethane elastomer in the resin components of the outer layer is preferably at least 5% by mass, more preferably at least 10% by mass, still more preferably at least 15% by mass, particularly preferably at least 20% by mass, and most preferably at least 25% by mass. The upper limit thereof may be 100% by mass or 100% by mass or less.

It is preferable that the inner layer composes primarily of the polyurethane elastomer. In this case, the content of the polyurethane elastomer in the resin components of the inner layer is preferably at least 50% by mass, more preferably at least 70% by mass, still more preferably at least 80% by mass, and particularly preferably at least 90% by mass. It is most preferable that all resin components of the inner layer are occupied by the polyurethane elastomer.

Elastomers other than the polyurethane elastomer are preferably a polyamide elastomer and/or a polyester elastomer.

Physical Property

The molecular weight of the elastomer to be applied is not particularly limited. The molecular weight is preferably from 10,000 to 1,000,000, more preferably from 20,000 to 500,000, and particularly preferably from 30,000 to 300,000, from the viewpoints that the elastomer constitutes a preferable hard segment and brings out a good interaction with a soft segment due to a chain extender.

In the present invention, the molecular weight of a polymer (including an elastomer) means a mass-average molecular weight, unless otherwise indicated. The mass-average molecular weight can be measured by polystyrene conversion in accordance with GPC.

Specifically, using a GPC instrument "HLC-8220" (trade name, manufactured by TOSOH CORPORATION), the measurement is carried out as follows. As an eluent, chloroform is used for a polyester elastomer, NMP (N-methyl-2-pyrrolidone) is used for a polyurethane elastomer, and m-cresol/chloroform (manufactured by Shonanwako Junyaku Co., Ltd.) is used for a polyamide elastomer. By using "TSKgel (G3000HXL+G2000HXL)" (trade name, manufactured by TOSOH CORPORATION) as a column, measurement is carried out under conditions of a measuring temperature of 23° C. and a flow rate of 1 mL/min. Detection is carried out using a RI detector.

As an eluent, NMP (N-methyl-2-pyrrolidone) is used for the ester-based urethane polymer in the adhesive of the present invention.

(Inner Layer)

Physical properties of the inner layer are preferably set to a suitable range.

For example, a Durometer D Hardness (JIS K7215) is preferably 40 or more, more preferably 50 or more, and particularly preferably 60 or more. The Durometer D is preferably 98 or less, more preferably 95 or less, and particularly preferably 90 or less.

A 100% modulus value is preferably 0.5 MPa or more, more preferably 1.0 MPa or more, and particularly preferably 1.5 MPa or more. The 100% modulus value is preferably 20 MPa or less, more preferably 15 MPa or less, and particularly preferably 10 MPa or less.

A storage modulus E' is preferably 1 MPa or more, more preferably 2 MPa or more, and particularly preferably 3 MPa or more. The storage modulus E' is preferably 150 MPa or less, more preferably 100 MPa or less, and particularly preferably 50 MPa or less.

A loss modulus E" is preferably 0.1 MPa or more, more preferably 0.3 MPa or more, and particularly preferably 0.5 MPa or more. The loss modulus E" is preferably 20 MPa or less, more preferably 10 MPa or less, and particularly preferably 5 MPa or less.

A loss tangent is preferably 0.01 or more, more preferably 0.03 or more, and particularly preferably 0.05 or more. The loss tangent is preferably 1 or less, more preferably 0.5 or less, and particularly preferably 0.3 or less.

(Outer Layer)

Physical properties of the outer layer are also preferably set to a suitable range.

For example, a Durometer D Hardness (JIS K7215) is preferably 20 or more, more preferably 25 or more, and particularly preferably 30 or more. The Durometer D Hardness (JIS K7215) is preferably 80 or less, more preferably 70 or less, and particularly preferably 60 or less.

A 100% modulus value is preferably 1.0 MPa or more, more preferably 1.5 MPa or more, and particularly preferably 2.0 MPa or more. The 100% modulus value is preferably 30 MPa or less, more preferably 25 MPa or less, and particularly preferably 20 MPa or less.

A storage modulus E' is preferably 1 MPa or more, more preferably 5 MPa or more, and particularly preferably 10 MPa or more. The storage modulus E' is preferably 1 GPa or less, more preferably 500 MPa or less, and particularly preferably 300 MPa or less.

A loss modulus E" is preferably 0.1 MPa or more, more preferably 0.5 MPa or more, and particularly preferably 1 MPa or more. The loss modulus E" is preferably 100 MPa or less, more preferably 50 MPa or less, and particularly preferably 30 MPa or less.

A loss tangent is preferably 0.01 or more, more preferably 0.03 or more, and particularly preferably 0.05 or more. The loss tangent is preferably 1 or less, more preferably 0.5 or less, and particularly preferably 0.3 or less.

In the present specification, the value relating to viscoelasticity means a value at 25° C., unless otherwise indicated. The measuring method is based on JIS K7244-4.

Further, in the present specification, the modulus value means a value at 25° C., unless otherwise indicated. The measuring method is based on JIS K7311.

The thickness of the resin layer is preferably equal to or less than 1000 µm, more preferably equal to or less than 800 µm, and particularly preferably equal to or less than 500 µm. There is no particular lower limit, but the lower limit is practically at least 200 µm.

[Top Coat]

To the flexible tube of the present embodiment, a top coat (coat layer) 16 is applied. A material of the top coat is not particularly limited and as the top coat material, a urethane coating material, an acrylic coating material, a fluorine coating material, a silicone coating material, an epoxy coating material, a polyester coating material, and the like are used. From the viewpoints that an adhesion property with a resin layer becomes remarkable, which is an advantage of the present embodiment, and also excellent chemical resistance is achieved, a urethane coating material, an acrylic coating material and a fluorine coating material are preferred.

A film of the top coat layer may be prepared by a usual method. Examples of the method include an embodiment of hardening a solution having the above top coat material dissolved in a predetermined solvent which contains a hardener, if needed.

Examples of the hardening treatment include heat at a temperature of 100 to 200° C.

A main purpose of use of the top coat in the present embodiment is the giving of protection, grazing, and a sliding property of the flexible tube surface, and the giving of chemical resistance.

Therefore, a top coat which exhibits a high elastic modulus, and makes its surface flat and smooth, and exhibits excellent chemical resistance, is preferred.

The storage elastic modulus E' of a single layer of the top coat is preferably at least 1 MPa, more preferably at least 5 MPa, and particularly preferably at least 10 MPa. The upper limit thereof is preferably equal to or less than 1 GPa, more preferably equal to or less than 500 MPa, and particularly preferably equal to or less than 300 MP.

By adjusting the storage elastic modulus E' to the above lower limit or greater, a surface-protective function of the top coat can be exerted. Further, by adjusting the storage elastic modulus E' to the above upper limit or less, flexibility of the flexible tube to be obtained can be maintained.

The thickness of the top coat layer is preferably reduced from the viewpoint of improving the performance of the resin layer. The thickness thereof is preferably equal to or less than 200 µm, more preferably equal to or less than 100 µm, and particularly preferably equal to or less than 50 µm. There is no particular lower limit, but the thickness is practically at least 10 µm.

In the above embodiment, a two-layered resin layer is formed in such an arrangement that a soft resin layer is placed as an inner layer while a rigid resin layer as an outer layer. The rigid resin layer may be placed as an inner layer while the soft resin layer as an outer layer.

Further, in the above embodiment, explanation is given about the two-layered outer coat layer as an example. The outer coat layer may have a multiple construction consisting of at least two layers and in the case of two layer constitution, other functional layers may lie between two layers.

In the above embodiment, explanation is given an electronic endoscope, as an example, which observes an image obtained by photographing the state of a subject to be examined, using an imaging device. However, the present invention is not limited to this embodiment, but can be also applied to an endoscope which observes the state of a subject to be examined, by adopting an optical image guide.

The flexible tube of the present invention is applied not only to an intended use of an endoscope, but also can be widely applied to an endoscope-type medical device. For example, the flexible tube also can be applied to an endoscope equipped with a clip or a wire at the head thereof, or a device equipped with a basket or a brush. In such devices, the flexible tube exhibits excellent effects.

Further, the method of producing an endoscope-type medical device through the method of producing a flexible tube for an endoscope of the present invention can manufacture an endoscope-type medical device having excellent operability which is suitable for a clinical examination by a doctor as well as reliability and durability due to the various properties of the flexible tube for an endoscope.

The term "endoscope-type medical device" is used in the sense of including broadly a medical/examination device which has flexibility and is introduced into a body to use it, such as remote-controlled medical device, in addition to medical device composed of the above-described endoscope as a basic structure.

EXAMPLES

The present invention will be described in more detail based on examples given below, but the invention is not meant to be limited by these. With regards to a blend amount or concentration, the term "part" or "%" is based on a mass standard, unless otherwise indicated.

[Synthesis of TPU-1]

To a 1 L three-necked flask, 15.0 g of 4,4'-diphenylmethane diisocyanate, 102.0 g of adipic acid, 179.4 g of 1,6-hexanediol, and dibutyl tin maleate as a catalyst were added, and the mixture was stirred at a system temperature of 220° C. for 30 minutes. Then, by increasing the system temperature to 250° C. and further stirring for 30 minutes, while distilling away 1,6-hexanediol under reduced pressure, an ester-based urethane polymer (TPU-1) having an urethane segment ratio of 7.89% and a mass-average molecular weight of 120,000 was synthesized.

25

[Synthesis of TPU-2]

To a 1 L three-necked flask, 10.0 g of 4,4'-diphenylmethane diisocyanate, 88.0 g of adipic acid, 20.0 g of polycaprolactone diol (trade name: PLACCEL L250AL, manufactured by Daicel Corporation, molecular weight: 500), 146.3 g of 1,6-hexanediol, and dibutyl tin maleate as a catalyst were added, and the mixture was stirred at a system temperature of 220° C. for 30 minutes. Then, by increasing the system temperature to 250° C. and further stirring for 30 minutes, while distilling away 1,6-hexanediol under reduced pressure, an ester-based urethane polymer (TPU-2) having an urethane segment ratio of 6.25% and a mass-average molecular weight of 125,000 was synthesized.

[Synthesis of TPU-3]

To a 1 L three-necked flask, 18.0 g of 4,4'-diphenylmethane diisocyanate, 73.0 g of adipic acid, 28.0 g of polypropylene glycol of diol type 400 (trade name, manufactured by Wako Pure Chemical Industries, Ltd.), 126.3 g of 1,6-hexanediol, and dibutyl tin maleate as a catalyst were added, and the mixture was stirred at a system temperature of 220° C. for 30 minutes. Then, by increasing the system temperature to 250° C. and further stirring for 30 minutes, while distilling away 1,6-hexanediol under reduced pressure, an ester-based urethane polymer (TPU-3) having an urethane segment ratio of 12.28% and a mass-average molecular weight of 130,000 was synthesized.

[Synthesis of TPU-4]

To a 1 L three-necked flask, 5.0 g of 4,4'-diphenylmethane diisocyanate, 146.0 g of adipic acid, 240.7 g of 1,6-hexanediol, and dibutyl tin maleate as a catalyst were added, and the mixture was stirred at a system temperature of 220° C. for 30 minutes. Then, by increasing the system temperature to 250° C. and further stirring for 30 minutes, while distilling away 1,6-hexanediol under reduced pressure, an ester-based urethane polymer (TPU-4) having an urethane segment ratio of 1.96% and a mass-average molecular weight of 120,000 was synthesized.

[Synthesis of TPU-5]

To a 1 L three-necked flask, 50.0 g of 4,4'-diphenylmethane diisocyanate, 102.0 g of adipic acid, 212.4 g of 1,6-hexanediol, and dibutyl tin maleate as a catalyst were added, and the mixture was stirred at a system temperature of 220° C. for 30 minutes. Then, by increasing the system temperature to 250° C. and further stirring for 30 minutes, while distilling away 1,6-hexanediol under reduced pressure, an ester-based urethane polymer (TPU-5) having an urethane segment ratio of 22.2% and a mass-average molecular weight of 120,000 was synthesized.

[Synthesis of TPU-6]

To a 1 L three-necked flask, 100.0 g of 4,4'-diphenylmethane diisocyanate, 73.0 g of adipic acid, 212.4 g of 1,6-hexanediol, and dibutyl tin maleate as a catalyst were added, and the mixture was stirred at a system temperature of 220° C. for 30 minutes. Then, by increasing the system temperature to 250° C. and further stirring for 30 minutes, while distilling away 1,6-hexanediol under reduced pressure, an ester-based urethane polymer (TPU-6) having an urethane segment ratio of 44.4% and a mass-average molecular weight of 100,000 was synthesized.

[Synthesis of TPU-7]

To a 1 L three-necked flask, 17.0 g of 1,6-hexamethylenediisocyanate, 102.0 g of adipic acid, 188.8 g of 1,6-hexanediol, and dibutyl tin maleate as a catalyst were added, and the mixture was stirred at a system temperature of 220° C. for 30 minutes. Then, by increasing the system temperature to 250° C. and further stirring for 30 minutes, while distilling away 1,6-hexanediol under reduced pressure, an ester-based urethane polymer (TPU-7) having an urethane segment ratio of 12.5% and a mass-average molecular weight of 100,000 was synthesized.

[Synthesis of TPU-8]

To a 1 L three-necked flask, 11.0 g of m-xylylene diisocyanate, 102.0 g of adipic acid, 179.4 g of 1,6-hexanediol, and dibutyl tin maleate as a catalyst were added, and the mixture was stirred at a system temperature of 220° C. for 30 minutes. Then, by increasing the system temperature to 250° C. and further stirring for 30 minutes, while distilling away 1,6-hexanediol under reduced pressure, an ester-based urethane polymer (TPU-8) having an urethane segment ratio of 7.89% and a mass-average molecular weight of 100,000 was synthesized.

[Synthesis of TPU-9]

To a 1 L three-necked flask, 10.0 g of 2,4-toluene diisocyanate, 116.0 g of isophthalic acid, 179.4 g of 1,6-hexanediol, and dibutyl tin maleate as a catalyst were added, and the mixture was stirred at a system temperature of 220° C. for 30 minutes. Then, by increasing the system temperature to 250° C. and further stirring for 30 minutes, while distilling away 1,6-hexanediol under reduced pressure, an ester-based urethane polymer (TPU-9) having an urethane segment ratio of 7.89% and a mass-average molecular weight of 100,000 was synthesized.

Example 1

<Preparation of Flexible Tube>

10.0 g of the above-synthesized ester-based urethane polymer TPU-1 was homogeneously dissolved into 125 g of methylethylketone (MEK) thereby preparing an adhesive solution. The adhesive solution was uniformly coated on a stainless-steel flexible tube substrate material having a length of 80 cm and a diameter of 12 mm and was dried at room temperature for 2 hours. Then, by subjecting the flexible tube substrate material to a thermal treatment at 150° C. for 2 hours, a flexible tube substrate having a dried adhesive adhered thereto was prepared.

Onto the flexible tube substrate material having the dried adhesive adhered thereto, an inner layer PU1 and an outer layer PU2 were applied by two-layer extrusion molding at a cylinder temperature of 200° C. in each extruder for 16 seconds as a time required for covering, in such a way that a volume ratio of the two-layers was 50/50 and each of the layer thickness was 0.2 mm (the total thickness of 0.4 mm). Thus, a resin-coated flexible tube No. 101 was prepared.

Hardening of the adhesive was promoted by heat at the time of extrusion thereby preparing an adhesive hardened.

Resin-coated flexible tube Nos. 102 to 109 and Nos. c11 to c13 were prepared using the above-synthesized ester-based urethane polymers TPU-2 to TPU-9 in the same manner as the preparation of the resin-coated flexible tube No. 101.

At this time, 1.1 g of each of polyisoxyanates PI-1 to PI-3 described in Table 1 was used so as to additionally add to the adhesive solution.

PU1 and PU2 each represent the following materials.

PU1: "MIRACTRAN E675MNAT" (75A), trade name, manufactured by Nippon Miractran Company Limited (mass-average molecular weight: 217,000, 100% modulus: 2.9 MPa)

PU2: "PANDEX T-2190" (92A), trade name, manufactured by DIC Bayer Polymer Ltd. (mass-average molecular weight: 189,000, 100% modulus: 11 MPa)

Further, PI-1, PI-2 and PI-3 each represent the following compositions.

PI-1: "CORONATE L" (75% ethyl acetate solution of trimethylolpropane adduct of 2,4-tolylenediisocyanate, number of isocyanate group in one molecule: 3, manufactured by Nippon Polyurethane Industry Co., Ltd., trade name), PI-2: "DURANATE TPA-100" (trimer of 1,6-hexamethylenediisocyanate, solid content: 100%, manufactured by Asahi Kasei Chemicals Corp., trade name)

PI-3: "CORONATE HXLV" (modified trimer of 1,6-hexamethylenediisocyanate, solid content: 100%, manufactured by Nippon Polyurethane Industry Co., Ltd., trade name)

[Calculation Method of Urethane Segment Ratio]

A ratio of a urethane segment equivalent (urethane segment ratio) with respect to the total equivalents of urethane segment and ester segment in the structures of the above-synthesized ester-based urethane polymers TPU-1 to TPU-9 was calculated by the formula below.

Herein, the term "urethane segment" means a urethane bond monomer unit composed of a diisocyanate compound and a diol compound. On the other hand, the term "ester segment" means an ester bond monomer unit composed of a diol compound and a dicarboxylic acid compound, or composed of a ring-open polymer of a cyclic ester compound.

The term "urethane segment equivalent ratio" means a molar ratio of the urethane segment.

$$\text{Urethane segment ratio (\%)} = \text{Urethane segment equivalent}/(\text{Urethane segment equivalent} + \text{Ester segment equivalent}) \times 100\%$$

For example, in the case of TPU-1, 4,4'-diphenylmethane diisocyanate:adipic acid=0.06:0.7 in molar ratio basis. As a result, the urethane segment ratio was as follows.

$$0.06/(0.06+0.7) \times 100 = 7.89\%$$

[Shore A Hardness]

The above-prepared adhesive solution was coated uniformly on a polyethylene terephthalate (PET) and dried at room temperature (25° C.) for 2 hours. Then, further by a thermal treatment at 150° C. for 2 hours, hardening of the adhesive was promoted thereby preparing an adhesive hardened. By peeling the PET from the adhesive hardened, a single film of the adhesive hardened was prepared.

The Shore A hardness of the prepared single film of the adhesive hardened was measured using a durometer based on JIS K7215.

The Shore A hardness of at least 70 and less than 100 is acceptable.

[Peeling Test]

With respect to the above-prepared flexible tube, a 1 cm-wide cut was made in the direction of the length of the resin and 90° peeling test was conducted, in which the resin layer was peeled off from a stainless-steel layer, and then a peeling strength was measured using a force gauge. The peeling strength of 15 N/cm was acceptable, preferably 20 N/cm or more, more preferably 30 N/cm or more.

[Resistance to Peracetic Acid]

Both ends of the above-prepared flexible tube were capped with a TEFLON (registered trademark) stopper and the flexible tube was immersed in a 0.3% peracetic acid aqueous solution at 55° C. for 150 hours and then a surface thereof was washed well. A peeling test was carried out in the same manner as the above and the peeling strength after immersion in the peracetic acid aqueous solution was measured. The peeling strength of at least 70% after immersion in the peracetic acid aqueous solution with respective to the peeling strength in the un-immersed state was ranked as "A". Likewise, the peeling strength of at least 60% and less than 70% was ranked as "B", the peeling strength of at least 50% and less than 60% was ranked as "C", and the peeling strength of less than 50% was ranked as "D".

The evaluations "A" and "B" each indicate a criteria of "excellent" in the peracetic acid resistance, and the evaluation "C" indicates a criteria of "usable", and the evaluation "D" indicates a criteria of "unusable".

[Resistance to Hydrogen Peroxide]

A hydrogen peroxide resistance test was carried out in the same manner as the peracetic acid resistance test, except that a 7.0% hydrogen peroxide solution was used in place of the 0.3% peracetic acid aqueous solution, and a peeling strength after immersion in the hydrogen peroxide solution was measured. The peeling strength of at least 70% after immersion in the hydrogen peroxide solution with respective to the peeling strength in the un-immersed state was ranked as "A". Likewise, the peeling strength of at least 60% and less than 70% was ranked as "B", the peeling strength of at least 50% and less than 60% was ranked as "C", and the peeling strength of less than 50% was ranked as "D".

The evaluations "A" and "B" each indicate a criteria of "excellent" in the hydrogen peroxide resistance, and the evaluation "C" indicates a criteria of "usable", and the evaluation "D" indicates a criteria of "unusable".

[Resilient Property]

Under the environment of temperature: 25° C. and relative humidity: 50%, the positions of 30 cm and 50 cm from one end portion of the above-prepared flexible tube were fixed, and the position of 40 cm (a central portion of the flexible tube) was compressed by 15 mm in a vertical direction (diameter direction) with respect to the length direction. A ratio of repulsion (B) after 30 seconds with respective to repulsion (A) after 0.1 seconds was defined as a resilient property (%), and the resilient property was measured.

$$[\text{Resilient property (\%)}] = (B)/(A) \times 100$$

The resilient property of at least 80% was ranked as "A". Likewise, the resilient property of at least 75% and less than 80% was ranked as "B", the resilient property of at least 65% and less than 75% was ranked as "C", and the resilient property of less than 65% was ranked as "D".

The evaluations "A" and "B" each indicate a criteria of "excellent" in the resilient property, and the evaluation "C" indicates a criteria of "usable", and the evaluation "D" indicates a criteria of "unusable".

[Bending Durability]

The above-prepared tube was placed in contact with a semicircular portion of the pulley having a diameter of 10 cm in a horseshoe shape and then the flexible tube was reciprocated 50,000 times in such a way that a tip portion and a rear-end portion thereof each get as near as 5 cm from the pulley end. Then, the state of the resin was visually observed.

The state in which none of float, tear and peeling was found in the resin was ranked as "A", the state in which float and/or peeling was found in a portion of less than 10% of the total resin was ranked as "B", the state in which float and/or peeling was found in a portion of at least 10% and less than 50% of the total resin was ranked as "C", the state in which float and/or peeling was found in a portion of at least 50% and less than 90% of the total resin was ranked as "D", and the state in which float and/or peeling was found in an area of at least 90% of the total resin was ranked as "E".

The evaluations "A" and "B" each indicate a category of "excellent" in the bending durability, and the evaluation "C" indicates a category of "usable", and the evaluation "D" indicates a category of "unusable".

The adhesive constitutions and evaluation results are shown together in Table 1.

Herein, Nos. 101 to 109 are flexible tubes using the adhesive of the present invention, while Nos. c11 to c13 are flexible tubes using the adhesive for comparison.

TABLE 1

| No. | Composition of adhesive | | Proportion of urethane segment (%) | Shore A hardness | Peeling strength [N/cm] | Resistance to peracetic acid | Resistance to hydrogen peroxide | Resilient property | Bending durability |
|---|---|---|---|---|---|---|---|---|---|
| | Ester-based urethane polymer | Polyisocyanate | | | | | | | |
| 101 | TPU-1 | — | 7.9 | 78 | 31 | B | B | A | B |
| 102 | TPU-1 | PI-1 | 7.9 | 95 | 52 | A | A | A | B |
| 103 | TPU-1 | PI-2 | 7.9 | 94 | 49 | A | A | A | B |
| 104 | TPU-1 | PI-3 | 7.9 | 90 | 51 | A | A | A | B |
| 105 | TPU-2 | PI-1 | 6.3 | 71 | 28 | B | A | C | A |
| 106 | TPU-3 | PI-1 | 12.3 | 72 | 32 | B | A | C | A |
| 107 | TPU-4 | PI-1 | 2.0 | 75 | 35 | B | B | C | A |
| 108 | TPU-5 | PI-1 | 22.2 | 85 | 26 | A | A | A | C |
| 109 | TPU-6 | PI-1 | 44.4 | 80 | 20 | A | A | A | C |
| c11 | TPU-7 | PI-1 | 12.5 | 60 | 12 | D | C | D | B |
| c12 | TPU-8 | PI-1 | 7.9 | 75 | 13 | C | D | A | C |
| c13 | TPU-9 | PI-1 | 7.9 | 73 | 13 | D | D | A | A |

The flexible tube coated with a resin using the adhesive of the present invention exhibited an excellent flexibility, a high chemical resistance, a high peeling strength, and an excellent resilient property. The flexible tube, therefore, has performances each of which is suitable for an endoscope-type medical device.

Further, the adhesive for an endoscope according to the present invention is also excellent in thermal stability at the time of molding in addition to the performances each of which is suitable for the endoscope-type medical device. As a result, the flexible tube for an endoscope and the endoscope-type medical device can be also preferably produced by using the adhesive for an endoscope of the present invention.

Having described our invention as related to the present embodiments, it is our intention that the invention not be limited by any of the details of the description, unless otherwise specified, but rather be construed broadly within its spirit and scope as set out in the accompanying claims.

REFERENCE SIGNS LIST

2 Electronic endoscope (Endoscope)
3 Insertion unit
3a Flexible tube
3b Angle portion
3c tip portion
5 Main body operating unit
6 Universal code
11 Spiral tube
11a Metal strip
12 Tubular mesh body
13 Cap
14 Fexible tube substrate
14a tip side
14b Rear anchor side
15 Resin layer
16 Coat layer
17 Inner layer
18 Outer layer
19 Layer of an adhesive hardened
20 Continuous molding machine (manufacturing apparatus)
21, 22 Extrusion sections
21a Screw
22a Screw
23 Head section
24 Cooling section
25 Conveying section
26 Controlling section
28 Feeding drum
29 Winding-up drum
30 Joint member
31 Connected flexible tube substrate material
32 Nipple
33 Dies
34 Support
35, 36 Gates
37 Mold pathway
38 Resin pathway
39 Flexible resin
40 Rigid resin
5a, 5b Metal strips
51 Spiral tube
56 Tubular mesh body (net)
57 Outer coat layer
A Sign showing the extrusion section 21 is controlled by the controlling section 26

The invention claimed is:

1. A flexible tube for an endoscope, comprising:
a tubular flexible tube substrate material having a flexibility; and
a resin layer covering the flexible tube substrate material,
wherein the resin layer is adhered to the flexible tube substrate material with an adhesive hardened,
wherein the adhesive hardened contains an ester-based polyurethane resin, which is a hardened resin of an adhesive for an endoscope,
wherein the adhesive for an endoscope contains an ester-based urethane polymer having a structure represented by the following Formula (1):

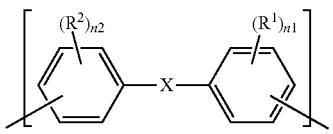

Formula (1)

wherein $R^1$ and $R^2$ each independently represent an alkyl group, an alkoxy group, an alkylthio group, an aryl group, or a halogen atom; n1 and n2 each independently represent an integer of 0 to 4; X represents —C($R^a$)($R^b$)—, —O—, —S—, —SO$_2$—, —C(=O)—, or —N($R^c$)—; $R^a$ and $R^b$ each independently represent a hydrogen atom, an alkyl group, or an aryl group; $R^c$ represents a hydrogen atom or an alkyl group; and $R^a$ and $R^b$ may be bonded to each other to form a ring, and wherein a surface material of the flexible tube substrate material is an aramid fiber, and wherein an equivalent ratio of an urethane segment with respect to a total of an urethane segment equivalent and an ester segment equivalent in the ester-based urethane polymer having a structure represented by the Formula (1) is at least 2% and less than 50%.

2. The flexible tube for an endoscope according to claim 1, wherein the ester-based polyurethane resin has a polyester structure, in which a diol compound and a dicarboxylic acid compound is being polymerized by condensation polymerization.

3. The flexible tube for an endoscope according to claim 1, wherein the ester-based polyurethane resin has a polyester structure, which is prepared by ring-opening polymerization of a cyclic ester compound.

4. The flexible tube for an endoscope according to claim 1, wherein an equivalent ratio of an urethane segment with respect to a total of an urethane segment equivalent and an ester segment equivalent in the ester-based polyurethane resin which is contained in the adhesive hardened containing the ester-based urethane polymer having a structure represented by the Formula (1) is 2% or more and less than 50%.

5. The flexible tube for an endoscope according to claim 1, wherein the ester-based polyurethane resin has a shore A hardness according to JIS K7215 of 70 or more and less than 100.

6. The flexible tube for an endoscope according to claim 1, wherein the ester-based polyurethane resin is a resin, in which the ester-based urethane polymer is hardened with a polyisocyanate compound having at least two isocyanate groups in one molecule thereof.

7. The flexible tube for an endoscope according to claim 1, wherein the ester-based urethane polymer has a mass average molecular weight of 50,000 or more and 500,000 or less.

8. The flexible tube for an endoscope according to claim 1, wherein the resin layer is composed of a single layer or plural layers, and at least the resin layer, which contacts with the flexible tube substrate material, contains a polyurethane elastomer.

9. The flexible tube for an endoscope according to claim 1, wherein the resin layer is composed of an inner layer and an outer layer and a thickness ratio of the inner layer and the outer layer varies slopewise in an axial direction of the flexible tube substrate material.

10. The flexible tube for an endoscope according to claim 9, wherein the thickness ratio of the inner layer and the outer layer is from 5:95 to 40:60 at one end of the flexible tube for an endoscope, wherein the thickness ratio of the inner layer and the outer layer is from 95:5 to 60:40 at the other end of the flexible tube for an endoscope, and wherein the thickness ratio is turned between both ends.

11. The flexible tube for an endoscope according to claim 1, wherein the flexible tube for the endoscope is used for an endoscope-type medical device.

12. An endoscope-type medical device, comprising the flexible tube for an endoscope according to claim 1.

13. The flexible tube for an endoscope according to claim 1, wherein the equivalent ratio is at least 2% and less than 20%.

14. The flexible tube for an endoscope according to claim 4, wherein the equivalent ratio is 2% or more and less than 20%.

15. A method of producing the flexible tube for an endoscope as claimed in claim 1, comprising the steps of:
preparing the flexible tube substrate material having an aramid fiber as a surface material thereof;
applying the adhesive for an endoscope to the surface of the flexible tube substrate material; and
covering the flexible tube substrate material to which the adhesive for an endoscope is being applied, with the resin layer.

16. The method of producing a flexible tube for an endoscope according to claim 15, wherein the resin layer comprises a polyurethane elastomer.

17. A method of producing an endoscope-type medical device, wherein the endoscope-type medical device is produced through the method of producing a flexible tube for an endoscope according to claim 15.

* * * * *